United States Patent
Kao et al.

(10) Patent No.: US 7,998,674 B2
(45) Date of Patent: Aug. 16, 2011

(54) GENE EXPRESSION PROFILING FOR IDENTIFICATION OF PROGNOSTIC SUBCLASSES IN NASOPHARYNGEAL CARCINOMAS

(75) Inventors: Kuo-jang Kao, Gainesville, FL (US); Andrew Huang, Durham, NC (US)

(73) Assignee: China Synthetic Rubber Corporation, Taipei (TW)

( * ) Notice: Subject to any disclaimer, the term of this patent is extended or adjusted under 35 U.S.C. 154(b) by 0 days.

(21) Appl. No.: 12/067,549

(22) PCT Filed: Sep. 22, 2006

(86) PCT No.: PCT/US2006/037203
§ 371 (c)(1),
(2), (4) Date: Jul. 23, 2008

(87) PCT Pub. No.: WO2007/038402
PCT Pub. Date: Apr. 5, 2007

(65) Prior Publication Data
US 2008/0281568 A1 Nov. 13, 2008

Related U.S. Application Data

(60) Provisional application No. 60/719,171, filed on Sep. 22, 2005, provisional application No. 60/721,129, filed on Sep. 28, 2005.

(51) Int. Cl.
*C12Q 1/68* (2006.01)
*C12N 15/12* (2006.01)
(52) U.S. Cl. .......................................... 435/6; 536/23.5
(58) Field of Classification Search ........................ None
See application file for complete search history.

(56) References Cited

U.S. PATENT DOCUMENTS
2003/0143539 A1 7/2003 Bertucci et al.

OTHER PUBLICATIONS

Dawkins, The Extended Phenotype, 1982, Oxford University Press, Oxford, pp. 85-86.*
Handbook of Chemistry and Physics, 49th Edition, Weast (ed.), The Chemical Rubber Co., Cleveland, OH, p. A-245.*
Alizadah et al, Nature 403: 503 (2000).*
An et al, Oral Oncology 40 (4), 400 (2004).*
Iizuka N. et al., "Oligonucleotide microarray for prediction of early intrahepatic recurrence of hepatocellular carcinoma after curative resection," The Lancet, vol. 361 No. 9361, Mar. 15, 2003, pp. 923-929, XP004764121.
Li Shen et al., "Dimension Reduction-Based Penalized Logistic Regression for Cancer Classification Using Microarray Data," IEEE/ACM Transactions on Computational Biology and Bioinformatics, vol. 2 No. 2, Apr. 2005, pp. 166-175, XP011133502.
Fang Wei-Yi et al., "Reexploring the Possible Roles of Some Genes Associated with Nasopharyngeal Carcinoma Using Microarray-Based Detection," Acta Biochemica et Biophysica Sinica Aug. 2005, vol. 37 No. 8, Aug. 2005, pp. 541-546, XP002421554.
Rhodes et al., "Integrative analysis of the cancer transcriptome", Nature Genetics Supplement, vol. 37, Jun. 2005, pp. 31-37.
Van 't Veer et al., "Gene expression profiling predicts clinical outcome of breast cancer", Naure, vol. 415, Jan. 31, 2002, pp. 530-536.

* cited by examiner

*Primary Examiner* — James Martinell
(74) *Attorney, Agent, or Firm* — Millen, White, Zelano, Branigan, P.C.

(57) ABSTRACT mRNA transcript profiling can be used to formulate molecular predictors of distant metastasis for primary NPCs. The predicted results are highly correlated with short metastasis-free and overall survival. Predictions are made using 52-genes based and 12-genes based predictors.

16 Claims, 8 Drawing Sheets

US 7,998,674 B2

GENE EXPRESSION PROFILING FOR IDENTIFICATION OF PROGNOSTIC SUBCLASSES IN NASOPHARYNGEAL CARCINOMAS

This application is a national stage entry of PCT/US2006/037203 filed Sep. 22, 2006, which claims the benefit of the filing date of U.S. Provisional Application Serial No. 60/719,171 filed Sep. 22, 2005 and U.S. Provisional Application Serial No. 60/721,129 filed Sep. 28, 2005, which are incorporated by reference herein.

The present invention relates generally to methods for evaluating and/or predicting nasopharyngeal cancer states and outcomes comprising measuring expression levels of genes related to such cancer, allowing individualized predictions or evaluations of outcomes for these cancer patients.

INTRODUCTION

Nasopharyngeal carcinoma (NPC) is a distinct type of head and neck cancer that differs from other malignancies of the upper aerodigestive tract with respect to epidemiology, pathology, clinical presentation and response to treatment.[1,2] The development of NPC is thought to be associated with infection of Epstein-Barr virus (EBV).[3,4] This type of cancer is endemic in southern China, Taiwan and southeast Asia (25-30 per 100,000 per year).[5-8] It is one of the more aggressive head and neck cancers which can infiltrate adjacent organs, invade retropharyngeal and cervical lymph nodes and disseminate to distant sites.[9-11]

The advancement of radiation therapy during the past three decades has led to the successful long-term control of NPC.[12-16] Radiation therapy is the indisputable mainstay of the NPC treatment. Patients with stage I and II disease have a high rate of cure with radiation therapy alone. Nevertheless, more than 70% of patients with newly diagnosed NPC have stage III and IV diseases.[14,17]. These patients require additional concurrent chemotherapy to improve their treatment outcome.[15,16] Furthermore, approximately 30% of NPC patients with stage III and IVa/b disease eventually develop distant metastasis,[14,17] i.e., metastasis outside the loco-regional area of the NPC. Ten to twenty percent of all NPC patients have distant metastasis and stage IVc diseases at the time of initial diagnosis.[14,17] Most patients die of the disease soon after the development of distant metastasis. Distant metastasis often takes place in the absence of loco-regional recurrence in stage III and IV NPC patients and is the most important prognostic factor.

The recent meta-analysis demonstrated that the improved survival in patients with advanced stages of NPC was likely the result of concurrent systemiic chemotherapy for probable prevention and controlling of distant metastasis.[15,16] Considering that more than 70% of NPC patients present with stage III and IV disease and about 30% of them may develop distant metastasis,[14,17] further improvement of survival in these patients has to begin with successful identification of patients at high risk for distant metastasis at initial presentation. When such prediction becomes a reality, currently optimized treatment can be applied and clinical trials can then be designed to test newer therapeutic modalities for more effective prevention and control of distant metastasis to improve overall survival.

Since the risk of distant metastasis is known to increase with more advanced stages of NPC[14,17], TNM staging has been used to guide the selection of suitable combinations of radiation therapy and chemotherapy for the prevention of distant metastasis and improvement of long term survival.[15,16,31] For instance, AJCC Stage III patients excluding those with T1N2M0 and T2aN2M0 disease have been treated with concurrent chemo-radiation therapy (CCRT) plus two cycles adjuvant chemotherapy with cisplatin plus 5-FU at Koo Foundation SYS Cancer Center, Taipei, Taiwan.[31] Stage IVa/b patients are treated with CCRT followed by 2 cycles of adjuvant chemotherapy and weekly maintenance chemotherapy with 5-FU and leucovorin for 6 months.[31] Although a significant number of patients with stage III disease responded well to the treatment and had excellent survival (FIG. 6), approximately 20% of stage III patients developed distant metastasis and had poor survival. The overall and the metastasis-free survival of the stage III patients who developed distant metastasis within three years of initial therapy were superimposed with those of stage IVa/b NPC patients (FIG. 6).

These findings raise the question whether stage III patients at risk of developing distant metastasis should have been treated more aggressively by neoadjuvant chemotherapy, newer or more intense adjuvant chemotherapy, and/or maintenance chemotherapy. The adequacy of treatment for stage IVa/b NPC patients at risk of developing distant metastasis is also called into question (FIG. 6). All these findings underscore the clinical importance of identification of NPC patients who are at risk of developing distant metastasis at the time of diagnosis and before initiation of treatment. Ability to identify such patients and to exclude stage III and IVa/b NPC patients who are low risk for distant metastasis are important for conducting more efficacious clinical trials.

As reported previously, microarray analyses have been successfully employed to identify molecular signatures for classification of tumors[18-22] and their clinical behavior[23-30], such as prediction of risks of distant metastasis and overall survival in patients with various types of malignancies. Other studies involve NPC.[37-54]

See also U.S. Application No. 60/420,729, filed Oct. 24, 2002; U.S. Application No. 60/421,102, filed Oct. 25, 2002; U.S. Application No. 60/421,062, filed Oct. 25, 2002; U.S. Application No. 60/424,701, filed Nov. 8, 2002; U.S. Application No. 60/424,718, filed Nov. 8, 2002; U.S. Application No. 60/424,715, filed Nov. 8, 2002; U.S. Application No. 60/425,256, filed Nov. 12, 2002; U.S. Application No. 60/448,462, filed Feb. 21, 2003; U.S. Application No. 60/448,466, filed Feb. 21, 2003; U.S. Application No. 60/457,877, filed Mar. 27, 2003; U.S. Application No. 60/458,373, filed Mar. 31, 2003; U.S. application Ser. No. 10/291,878, filed Nov. 12, 2002; U.S. application Ser. No. 10/291,886, filed Nov. 12, 2002; International Application No. US02/38216, filed Nov. 12, 2002; and International Application No. US02/38222, filed Nov. 12, 2002; U.S. application Ser. No. 11/015,764, filed Dec. 20, 2004; U.S. application Ser. No. 11/090,294, filed Mar. 28, 2005 and U.S. Provisional Application No. 60/665,652, filed Mar. 25, 2005, the entire disclosures of all of which are incorporated herein-by reference for details on methodology used herein.

SUMMARY OF THE INVENTION

This invention identifies genomic signatures for distant metastasis in NPC patients. The improved prediction which results for distant metastasis in NPC patients enables one to identify individual patients at high risk for whom suitable therapies (e.g., radiation and/or chemotherapy) can be selected for the prevention and/or amelioration of distant metastasis and improvement of long term survival. Thus, in one aspect, this invention involves a method of correlating gene expression levels in NPC patients to risk factors and clinical outcomes in said patients.

Thus, the invention relates to a method of assessing the risk of distant metastasis in a patient having nasopharyngeal carcinoma comprising evaluating the expression profile of at least one of the genes listed in Tables 4 and 5 below in a sample from said patient. Preferably, essentially all and especially all of the 52 genes of Table 4 and/or essentially all and especially all of the 12 genes of Table 5 are evaluated for expression levels, e.g., in patient samples, preferably NPC tissue samples. Thus, two or more of the genes of Tables 4 or 5 can be employed as long as the number of genes assessed for probability analysis are correlated with disease outcome (e.g., distant metastasis). In other embodiments, for the 12 gene set, 3 or more, 4 or more, 5 or more, 6 or more, 7 or more, 8 or more, 9 or more, 10 or more, or 11 or more of the genes can be employed. Such numbers of genes can also be employed with respect to the 52 gene set, or 12 or more . . . 15 or more . . . 20 or more . . . 25 or more . . . 30 or more . . . 35 or more . . . 40 or more . . . 45 or more . . . 50 or more . . . 51 or more, as well as other encompassed numbers of genes not explicitly mentioned here. Such numbers of genes from each set can also be employed in the combination method discussed below. Of course, for optimal results, all or essentially all genes will be employed in general. Thus, in another aspect, the genes used in the foregoing methods are one or more of those listed herein.

This invention also relates to collections, e.g., in media or kits, etc., of all or subsets of such genes related to distant metastasis; and it relates to associated methods, media and kits used in carrying out the methods of this invention.

In accordance with another aspect of the invention, the patient speciment analyzed may be any tissue such as blood, tumors or cells, etc. Preferably, the specimen is from an NPC tumor. Methods for obtaining a specimen to be analyzed are known in the art.

The subject invention provides collections of genes that are relevant for the evaluation or prediction of distant metastasis in an NPC patient. Such genes have an expression pattern (i.e., level expression or lack thereof) that correlates with at least one such cancer phenotype. It is understood that additional genes may also be involved in NPC.

For this invention, a gene expression profiling study was conducted on banked biopsy specimens from NPC patients who had well documented clinical data. All biopsy samples studied were stored in liquid nitrogen. Only samples without significant degradation of total RNA were studied. In order to minimize the operator-related variation, only two highly trained technicians were involved in the processing of tumor samples and collection of microarray data. They randomly handled similar numbers of specimens from patients with high or low risk of distant metastasis. Statistical analyses of microarray data performed and collected by both technical personnel did not show any statistical bias (FIG. 7). We also used the same fluidic station and the same scanner throughout the study.

In order to further minimize variations associated with chip manufacturing, sample processing, loading doses of cRNA and chip processing, gene expression intensity data of each microarray were normalized to a trimmed mean of 500 using Affymetrix MAS 5.0 software and followed by quantile normalization of the expression intensity of each probe set according to a NPC reference standard previously established in our laboratory. See Example I. The effectiveness of such normalization approach was validated by comparison of the GeneChip results of repeated measurements on six randomly selected NPC specimens. The results showed that the qauntile normalization procedure at probe set level was indeed effective to correct the experimental variations (FIG. 8).

A highly supervised analysis was performed. As discussed earlier, most NPC patients without the development of distant metastasis in three years after the initial treatment have good long term survival, and NPC patients of poor survival outcome usually develop distant metastases within three years after the first treatment. Biopsy specimens from these two groups of clinically well defined patients at opposite ends of the disease were used in the analysis to identify more reliable molecular signatures for prediction of distant metastasis. The benefit of taking such an approach for finding reliable molecular predictors was reported recently.[35]

At the same time, overfitting is a serious pitfall for finding class predictors from a limited number of patients with high dimensional measurements as articulated by Simon et al.[36] To overcome the overfitting problem, a truly independent test set of cases for validation was included and as many patients as possible were included in the study. One hundred thirty eight eligible patients were included. Moreover, a third of patients from low and high risk groups of patients were randomly assigned to an independent test set at the very beginning of the study for validation purposes. Important clinical variables, such as age, gender, tumor stage, follow up durations were considered for randomization. All test set cases were not involved in the selection of predictor genes and the establishment of predictive rules throughout the training process. The results of this invention on the test set showed that the sensitivity, the specificity and the overall accuracy were comparable to or better than what have been reported for other types of solid tumors in the literature.[23,24,27-30]

The quantities of viable tumor cells and surrounding lymphoid/inflammatory/stromal cells can significantly vary between biopsy specimens of different patients (biological heterogeneity). Due to very limited quantities of biopsy tissues available and the instability of RNA, histological examination of the biopsy specimens used for gene expression profiling, however, was not performed. Also, the histology of the diagnostic biopsy specimens was not correlated with the accuracy of the predicted results because the biopsy sites for diagnosis and for GeneChip study were not identical. Noise associated with heterogeneity of biopsy specimens could limit predictive accuracy.

Two preferred predictive rules are generated by this invention. See Examples IV and V. One is based on the signature of 52 genes and k-NN classifying method, and the other is based on 12 genes and logistic regression.

In one set, fifty two genes from nine different SOM clusters are used for prediction. They are summarized in Table 4. Among these 52 genes, are members involved in signal transduction (n=9), mRNA processing (n=7), transcription regulation (n=3), protein synthesis (n=4), nucleotide metabolism (n=4), lipid metabolism (n=3), protein folding (n=3), cytokinesis (n=2), nuclear transport (n=2), protein catabolism (n=2), anti-apoptosis (n=1), ATP snthesis (n=1), cell cycle (n=1), immune response (n=1), intracellular protein transport (n=1) and amino acid transport (n=1), according to the NIAID-DAVID Tools (http://apps1.niaid.nih.gov/david/). Function of the remaining seven genes was unknown.

Twenty two of the 52 genes had reduced expression and thirty had increased expression in the high risk group. When the expression intensities of predictor genes between the high and the low risk groups were compared, it could be noted that the average expression of almost all genes involved in mRNA processing, nuclear transport, nucleotide metabolism, and protein folding was greater in the predicted high risk group. In contrast, the expression of all genes involved in transcription regulation and protein catabolism was reduced in the group predicted as high risk for distant metastasis.

For the predictive method based on the 12 genes, 6 genes were also present in the 52 genes used for prediction by a k-NN method. The other six were not present in the list of the 52 genes according to Affymterix probe set ID. These 12 genes are summarized in Table 5. Among these 12 genes, 3 genes were involved in protein folding, 2 genes in protein synthesis, 2 genes in ribosome biogenesis, 2 genes in nucleotide metabolism, and 1 gene each in mRNA processing and protein catabolism. The last gene (hypothetical protein FLJ12671) was known to have nucleolar exonuclease motif and its exact function was not known. The functions of all 12 genes showed significant overlap with those in the set of 52 genes. It was noted that one of the six genes (non-POU domain containing protein) that was not included in any of the 52 genes was actually the same as the gene represented by a different probe set ID in the 52 genes. This gene is involved in mRNA processing. Three genes in the 12-genes set are alpha, beta and gamma subunits of the same chaperonin containing t-complex 1 (TCP-1) that has been implicated in the proliferation of tumor cells.[34] The genes for the subunits alpha and gamma were present in both the 12- and the 52-gene set. The gene for the subunit beta was present only in the 12-genes set. All these findings showed a high degree of consistency between these two sets of predictor genes.

The results of the use of the predictive rules show that the method of 52-genes prediction had a lower false positive rate than the method of 12-genes prediction (14% vs 28%). In contrast, the method of 52-genes prediction had a higher false negative rate than the method of 12-genes (31% vs 15%). When the predictive methods are used to select patients with high risk of distant metastasis for clinical trials, false positive and false negative rates will be reduced to a minimum so that the safety of low risk patients and the right of high risk patients are protected.

For example, the two methods for prediction can be combined in one method. Only results of concordance between the two methods are accepted. Results of discordance are regarded as indeterminate (n=8). See Example VI. By taking such an approach, the false positive rate was reduced to 10%. The false negative rate was around 15%. Although the indeterminate cases accounted for 19% (8/42) of all patients in the independent test set, only 2 clinically high risk patients were assigned to the indeterminate category by the combined use of molecular predictors. In this manner, chances of falsely including good risk patients into a trial for the high risk patients could be effectively minimized at the expense of excluding 15% (2/13) of clinically high risk patients. The other 15% of clinically high risk patients will be incorrectly predicted as low risk (Table 6). Nevertheless, at least 70% of all high risk patients will be correctly identified and may be included in trials designed for high risk patients.

Thus, reliable molecular signatures of 52-genes and 12-genes have been identified to predict NPC patients at high or low risk of developing distant metastasis. The prediction is validated with 42 independent test set cases. The overall accuracies assessed by the independent test set were 81%, 76% and 85% for the 52-genes signature, the 12-genes signature and the combined signature, respectively. These results are comparable to the recently published predictive studies that also used independent test sets for validation.[28,30] An accuracy of 78% was reported for prediction of breast cancer response to neoadjuvant chemotherapy[28] and an accuracy of 86% for prediction of lymph node metastasis by head-and-neck squamous cell carcinoma.[30] The molecular signatures will be useful to guide new neoadjuvant, adjuvant, maintenance chemotherapy and/or targeted-therapy in NPC patients for prevention, amelioration and control of distant metastasis and for further improvement of long term survival. The identification of NPC patients with low or high risk for distant metastasis also should reduce the rates of over- and under-treatment.

The subject collections of NPC metastasis related genes may be physical or virtual. Physical collections are those collections that include a population of different nucleic acid molecules, where the NPC cancer related genes are represented in the population, i.e., there are nucleic acid molecules in the population that correspond in sequence to the genomic, or more typically, coding sequence of the NPC cancer related genes in the collection. In many embodiments, the nucleic acid molecules are either substantially identical or identical in sequence to the sense strand of the gene to which they correspond, or are complementary to the sense strand to which they correspond, typically to an extent that allows them to hybridize to their corresponding sense strand under stringent conditions. Determining hybridization conditions (i.e., low, medium, or high stringency) is within the knowledge of the skilled artisan. An example of stringent hybridization conditions is hybridization at 50° C. or higher and 0.1 SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed to identify nucleic acids of this particular embodiment of the invention.

The nucleic acids that make up the subject physical collections may be single-stranded or double-stranded. In addition, the nucleic acids that make up the physical collections may be linear or circular, and the individual nucleic acid molecules may include, in addition to NPC cancer related genes, other sequences, e.g., vector sequences. A variety of different nucleic acids may make up the physical collections, e.g., libraries, such as vector libraries, of the subject invention, where examples of different types of nucleic acids include, but are not limited to, DNA, e.g., cDNA, etc., RNA, e.g., mRNA, cRNA, etc. and the like. The nucleic acids of the physical collections may be present in solution or affixed, i.e., attached to, a solid support, such as a substrate as is found in array embodiments, where further description of such diverse embodiments is provided below.

Also provided are virtual collections of the subject NPC related genes. By virtual collection is meant one or more data files or other computer readable data organizational elements that include the sequence information of the genes of the collection, where the sequence information may be the genomic sequence information but is typically the coding sequence information. The vial collection may be recorded on any convenient computer or processor readable storage medium. The computer or processor readable storage medium on which the collection data is stored may be any convenient medium, including CD, DAT, floppy disk, RAM, ROM, etc, which medium is capable of being read by a hardware component of the device.

Also provided are databases of expression profiles of NPC related genes. Such databases will typically comprise expression profiles of various cells/tissues having NPC related phenotypes, such as various stages of NPC, negative expression profiles, prognostic profiles, etc., where such profiles are further described below.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. One format for an output means ranks expression profiles possessing varying degrees of similarity to a reference expression profile. Such presentation provides a skilled artisan with a ranking of similarities and identifies the degree of similarity contained in the test expression profile.

A gene expression profile can be measured at a single time point or cover several time points over a period of time. The expression levels of the genes can be determined by any method known in the art (e.g., quantitative polymerase chain reaction (PCR), reverse transcriptase/polymerase PCR) or that is devised in the future that can provide quantitative information regarding gene expression.

In another embodiment, gene expression levels are determined by quantitating gene expression products such as proteins, polypeptides or nucleic acid molecules (e.g., mRNA, tRNA, rRNA). Quantitating nucleic acid can be performed by quantitating the nucleic acid directly or by quantitating a corresponding regulatory gene or regulatory sequence element. Additionally, variants of genes such as splice variants and polymorphic variants can be quantitated.

In another embodiment, gene expression is measured by quantitating the level of protein or polypeptide translated from mRNA. Methods for quantitating the level of protein or polypeptide in a sample and correlating such data with expression levels are known in the art. For example, polyclonal or monoclonal antibodies specific for a protein or polypeptide can be obtained by methods known in the art and used to detect and/or measure the protein or polypeptide in the sample or specimen.

In a preferred embodiment, gene expression is measured by quantitating the level of mRNA in a sample or specimen. This can be carried out by any of the known methods in the art. In one embodiment, mRNA is contacted with a suitable microarray comprising immobilized nucleic acid probes specific for the genes of interest and determining the extent of hybridization of the mRNA in the sample to the probes on the microarray. Such microarrays are also within the scope of the invention. Examples of methods of making oligonucleotide microarrays are described, for example, in WO 95/11995. Other methods are readily known in the art.

The gene expression value measured or assessed is the numeric value obtained from an apparatus that can measure gene expression levels. The values are raw values from the apparatus, or values that are preferably re-scaled, filtered and/or normalized. See, e.g., Example I. Nucleic acids (e.g., mRNA) from a sample that has been subjected to particular stringency conditions hybridize to the probes on the chip. The nucleic acid to be analyzed (e.g., the target) is isolated, amplified and labeled with a detectable label, (e.g., $^{32}P$ or fluorescent label) prior to hybridization to the arrays. After hybridization, the arrays are inserted into a scanner that can detect patterns of hybridization. These patterns are detected by detecting the labeled target now attached to the microarray, e.g., if the target is fluorescently labeled, the hybridization data are collected as light emitted from the labeled groups. Since labeled targets hybridize, under appropriate stringency conditions known to one of skill in the art, specifically to complementary oligonucleotides contained in the microarray, and since the sequence and position of each oligonucleotide in the array are known, the identity of the target nucleic acid applied to the probe is determined.

The present invention also provides a method for monitoring the effect of a treatment regimen in an individual by monitoring the gene expression profiles of the invention. For example, a baseline gene expression profile for the individual can be determined, and repeated gene expression profiles can be determined at time points during treatment. A shift in gene expression profile from a profile correlated with poor treatment outcome to a profile correlated with improved treatment outcome is evidence of an effective therapeutic regimen, while a repeated profile correlated with poor treatment outcome is evidence of an ineffective therapeutic regimen.

In diagnostic applications of the subject invention, cells or collections thereof, e.g., tissues, as well as animals (subjects, hosts, etc., e.g., mammals, such as pets, livestock, and humans, etc.) that include the cells/tissues are assayed to determine the presence of and/or probability for development of an NPC metastasis. As such, diagnostic methods include methods of determining the presence of such a phenotype. In certain embodiments, not only the presence but also the severity or stage of a phenotype is determined. In addition, diagnostic methods also include methods of determining the propensity to develop such a cancer phenotype, such that a determination is made that such cancer phenotype is not present but is likely to occur. In practicing the subject diagnostic and other methods, a nucleic acid sample obtained or derived from a cell, tissue or subject that is to be diagnosed is assayed to generate an expression profile and then the method of the invention is carried out.

As indicated above, the sample that is assayed to generate the expression profile employed in the diagnostic methods is one that is a nucleic acid sample. The nucleic acid sample includes a plurality or population of distinct nucleic acids that includes the expression information of the NPC related genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample is typically prepared from a cell or tissue harvested from a subject to be diagnosed, e.g., via biopsy of tissue, using standard protocols, where cell types or tissues from which such nucleic acids may be generated include any tissue in which the expression pattern of the to be determined NPC phenotype exists, including, but not limited, to, monocytes, endothelium, and/or smooth muscle.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143, 854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO97/10365; WO 97/27317; EP 373 203; and EP 785 280. In these methods, an array of "probe" nucleic acids that includes a probe for each of the NPC related genes whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acid provides information regarding expression for each of the genes that have been probed, where the expression information is in terms of whether or not the gene is expressed and, typically, at what level, where the expression data, i.e., expression profile, may be both qualitative and quantitative.

In many embodiments, the above obtained information about the cell/tissue being assayed is employed to diagnose a host, subject or patient with respect to the presence of, state of or propensity where already developed, to predict course and outcomes. For example, where the cell/tissue that is assayed is determined to have a NPC metastasis phenotype, the information may be employed to diagnose a subject from which the cell/tissue was obtained as having cancer recurrence probability.

In addition to monitoring the effectiveness of a particular treatment, the present invention can be applied to screen potential drug candidates for their efficacy in treating NPC metastasis likelihood. In this embodiment, a sample's expression profile is compared before and after treatment with the candidate drug, wherein a shift in the gene expression profile in the treated sample from a profile correlated with poor treatment outcome to a profile correlated with improved treatment outcome is evidence for the efficacy of the drug. Such assays can be performed in vitro or in animal models using conventional procedures.

Another application in which the subject collections of NPC related genes find use is in monitoring or assessing a given treatment protocol. In such methods, a cell/tissue sample of a patient undergoing treatment is monitored using the procedures described herein where the obtained expression profile(s) is compared to one or more reference profiles to determine whether a given treatment protocol is having a desired impact on the disease being treated. For example, periodic expression profiles are obtained from a patient during treament and compared to a series of reference/controls that includes expression profiles of various NPC metastasis stages and normal expression profiles. An observed change in the monitored expression profile towards a normal profile indicates that a given treatment protocol is working in a desired manner.

Therapeutic Agent Screening Applications

The present invention also encompasses methods for identification of agents having the ability to modulate the NPC metastasis phenotype, e.g., enhance or diminish it, which finds use in identifying therapeutic agents.

Identification of compounds that modulate such phenotype can be accomplished using any of a variety of drug screening techniques. The screening assays of the invention are generally based upon the ability of the agent to modulate an expression profile of NPC metastasis phenotype determinative genes.

The term "agent" as used herein describes any molecule, e.g., protein, small molecule or other pharmaceutical, with the capability of modulating a biological activity of a differentially expressed gene product. Generally a plurality of assay mixtures are run in parallel with different agent concentrations to obtain a different response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 50 and less than 2,500 daltons. Candidate agents often comprise functional groups necessary for structural interaction with proteins, particularly hydrogen bonding, and often include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts (including extracts from human tissue to identify endogenous factors affecting differentially expressed gene products) are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Exemplary candidate agents of particular interest include, but are not limited to, antisense polynucleotides, and antibodies, soluble receptors, and the like. Antibodies and soluble receptors are of particular interest as candidate agents where the target differentially expressed gene product(s) is secreted or accessible at the cell-surface (e.g., receptors and other molecule stably-associated with the outer cell membrane).

Screening assays can be based upon any of a variety of techniques readily available and known to one of ordinary skill in the art. In general, the screening assays involve contacting a cell or tissue known to have NPC metastasis phenotype with a candidate agent, and assessing the effect upon a gene expression profile made up of phenotype determinative genes. The effect can be detected using any convenient protocol, where in many embodiments the diagnostic protocols described above are employed. Generally such assays are conducted in vitro, but many assays can be adapted for in vivo analyses, e.g., in an animal model of the cancer.

Screening for Drug Targets

In another embodiment, the invention contemplates identification of genes and their products, from the lists herein as therapeutic targets. In some respects, this is the converse of the assays described above for identification of agents having activity in modulating (e.g., decreasing or increasing) an NPC metastasis phenotype, and is directed towards identifying genes that are particularly phenotype determinative, or their expression products, as therapeutic targets.

In this embodiment, therapeutic targets are identified by examining the effect(s) of an agent that can be demonstrated or has been demonstrated to modulate an NPC phenotype (e.g., inhibit or suppress such phenotype). For example, the agent can be an antisense oligonucleotide that is specific for a selected gene transcript. For example, the antisense oligonucleotide may have a sequence corresponding to a sequence of a gene appearing in the tables herein.

Assays for identification of therapeutic targets can be conducted in a variety of ways using methods that are well known to one of ordinary skill in the art. For example, a test cell that expresses or overexpresses a candidate gene, e.g., a gene found in tables herein contacted with the known NPC agent, and the effect upon a NPC phenotype and a biological activity of the candidate gene product assessed. The biological activity of the candidate gene product can be assayed be examining, for example, modulation of expression of a gene encoding the candidate gene product (e.g., as detected by, for example, an increase or decrease in transcript levels or polypeptide levels), or modulation of an enzymatic or other activity of the gene product.

Inhibition or suppression of the NPC metastatsis phenotype indicates that the candidate gene product is a suitable target for therapy. Assays described herein and/or known in the art can be readily adapted in for assays for identification of therapeutic targets. Generally such assays are conducted in vitro, but many assays can be adapted for in vivo analyses, e.g., in an appropriate, art-accepted animal model.

Reagents and Kits

Also provided are reagents and kits thereof for practicing one or more of the above described methods. The subject reagents and kits thereof may vary greatly. Reagents of interest include reagents specifically designed for use in production of the above described expression profiles of NPC phenotype determinative genes.

One type of such reagent is an array of probes of nucleic acids in which the NPC metastasis phenotype determinative genes of interest are represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In many embodiments, the arrays include probes for at least 2 of the genes listed herein. In certain embodiments, the number of genes represented on the array is at least 5, at least 10, at least 25, at least 50, or more, including all of the genes listed herein. The subject arrays may include only those genes that are listed herein, or they may include additional genes that are not listed herein. Where the subject arrays include probes for such additional genes, in certain embodiments the number % of additional genes that are represented does not exceed about 50%, usually does not exceed about 25%. In many embodiments where such additional genes are included, a great majority of the genes in the collection will be NPC cancer phenotype determinative genes, where by great majority is meant at least about 75%, usually at least about 80% and sometimes at least about 85, 90, 95% or higher, including embodiments where 100% of the genes in the collection are NPC cancer phenotype determinative genes. In many embodiments, at least one of the genes represented on the array is a gene whose function does not readily implicate it in the production of an NPC cancer phenotype.

Another type of reagent that is specifically tailored for generating expression profiles of NPC cancer phenotype determinative genes is a collection of gene specific primers that is designed to selectively amplify such genes. Gene specific primers and methods for using the same are described in U.S. Pat. No. 5,994,076, the disclosure of which is herein incorporated by reference. Of particular interest are collections of gene specific primers that have primers for at least 2 of the genes listed herein. In certain embodiments, the number of such genes that have primers in the collection is at least 5, at least 10, at least 25, at least 50, or more, including all of the genes listed herein. The subject gene specific primer collections may include only those genes that are listed herein, or they may include primers for additional genes that are not listed herein. Where the subject gene specific primer collections include primers for such additional genes, in certain embodiments the number % of additional genes that are represented does not exceed about 50%, usually does not exceed about 25%. In many embodiments where such additional genes are included, a great majority of genes in the collection are NPC phenotype determinative genes, where by great majority is meant at least about 75%, usually at least about 80% and sometimes at least about 85, 90, 95% or higher, including embodiments where 100% of the genes in the collection are NPC phenotype determinative genes. In many embodiments, at least one of the genes represented on a collection of gene specific primers is a gene whose function does not readily implicate it in the production of an NPC cancer phenotype.

The kits of the subject invention may include the above described arrays and/or gene specific primer collections. The kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Compounds and Methods For Treament Of NPC Metastasis

Also provided are methods and compositions whereby NPC metastasis likelihood may be ameliorated. The subject invention provides methods of ameliorating, e.g., treating such conditions, by modulating the expression of one or more target genes or the activity of one or more products thereof, where the target genes are one or more of the NCP phenotype determinative genes listed herein.

Certain NPC disease states are brought about, at least in part, by an excessive level of gene product(s), or by the presence of a gene product(s) exhibiting an abnormal or excessive activity. As such, the reduction in the level and/or activity of such gene products would bring about the amelioration of disease recurrence. Techniques for the reduction of target gene expression levels or target gene product activity levels are discussed below.

Alternatively, certain other NPC disease states are brought about, at least in part, by the absence or reduction of the level of gene expression, or a reduction in the level of a gene product activity. As such, an increase in the level of gene expression and/or the activity of such gene products would bring about the amelioration of disease. Techniques for increasing target gene expression levels or target gene product activity levels are discussed below.

Compounds that Inhibit Expression, Synthesis or Activity of Mutant Target Gene Activity As discussed above, target genes involved in NPC disease disorders can cause such disorders via an increased level of target gene activity. Where a gene is up-regulated in cells/tissues under disease conditions, a variety of techniques may be utilized to inhibit the expression, synthesis, or activity of such target genes and/or proteins. For example, compounds such as those identified through assays described which exhibit inhibitory activity, may be used in accordance with the invention to ameliorate disease symptoms. As discussed above, such molecules may include, but are not limited to small organic molecules, peptides, antibodies, and the like. Inhibitory antibody techniques are described, below.

For example, compounds can be administered that compete with an endogenous ligand for the target gene product, where the target gene product binds to an endogenous ligand. The resulting reduction in the amount of ligand-bound gene target will modulate endothelial cell physiology. Compounds that can be particularly useful for this purpose include, for example, soluble proteins or peptides, such as peptides comprising one or more of the extracellular domains, or portions and/or analogs thereof, of the target gene product, including, for example, soluble fusion proteins such as Ig-tailed fusion proteins. (For a discussion of the production of Ig-tailed fusion proteins, see, for example, U.S. Pat. No. 5,116,964.). Alternatively, compounds, such as ligand analogs or antibodies, that bind to the target gene product receptor site, but do not activate the protein, (e.g., receptor-ligand antagonists) can be effective in inhibiting target gene product activity. Furthermore, antisense and ribozyme molecules which inhibit expression of the target gene may also be used in accordance with the invention to inhibit the aberrant target gene activity. Such techniques are described, below. Still further, also as described, below, triple helix molecules may be utilized in inhibiting the aberrant target gene activity.

Inhibitory Antisense, Ribozyme and Triple Helix Approaches

Among the compounds which may exhibit the ability to ameliorate NPC metastasis are antisense, ribozyme, and triple helix molecules. Such molecules may be designed to reduce or inhibit mutant target gene activity. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred. Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding target gene proteins. Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays. Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex. Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyridines to be present on one strand of a duplex. It is possible that the antisense, ribozyme, and/or triple helix molecules described herein may reduce or inhibit the transcription (triple helix) and/or translation (antisense, ribozyme) of mRNA produced by both normal and mutant target gene alleles. In order to ensure that substantially normal levels of target gene activity are maintained, nucleic acid molecules that encode and express target gene polypeptides exhibiting normal activity may be introduced into cells via gene therapy methods such as those described, below, that do not contain sequences susceptible to whatever antisense, ribozyme, or triple helix treatments are being utilized. Alternatively, it may be preferable to co-administer normal target gene protein into the cell or tissue in order to maintain the requisite level of cellular or tissue target gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Antibodies for Target Gene Products

Antibodies that are both specific for target gene protein and interfere with its activity may be used to inhibit target gene function. Such antibodies may be generated using standard techniques known in the art against the proteins themselves or against peptides corresponding to portions of the proteins. Such antibodies include but are not limited to polyclonal, monoclonal, Fab fragments, single chain antibodies, chimeric antibodies, etc.

In instances where the target gene protein is intracellular and whole antibodies are used, internalizing antibodies may be preferred. However, lipofectin liposomes may be used to deliver the antibody or a fragment of the Fab region which binds to the target gene epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (e.g., see Creighton, 1983, supra; and Sambrook et al., 1989, supra). Alternatively, single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889-7893).

In some instances, the target gene protein is extracellular, or is a transmembrane protein. Antibodies that are specific for one or more extracellular domains of the gene product, for example, and that interfere with its activity, are particularly useful in treating breast cancer disease. Such antibodies are especially efficient because they can access the target domains directly from the bloodstream. Any of the administration techniques described, below which are appropriate for peptide administration may be utilized to effectively administer inhibitory target gene antibodies to their site of action.

Methods for Restoring Target Gene Activity

Target genes that contribute to NPC metastasis may be underexpressed within disease situations. Where a gene is down-regulated under disease conditions or the activity of target gene products are diminished, leading to the development of disease symptoms, methods can be used whereby the level of target gene activity may be increased to levels wherein NPC disease symptoms are ameliorated. The level of gene activity may be increased, for example, by either increasing the level of target gene product present or by increasing the level of active target gene product which is present.

For example, a target gene protein, at a level sufficient to ameliorate NPC metastases may be administered to a patient exhibiting such symptoms. Any of the techniques discussed, below, may be utilized for such administration. One of skill in the art will readily know how to determine the concentration of effective, non-toxic doses of the normal target gene protein, utilizing techniques such as those described below.

Additionally, RNA sequences encoding target gene protein may be directly administered to a patient exhibiting NPC metastases, at a concentration sufficient to produce a level of target gene protein such that such symptoms are ameliorated. Any of the techniques discussed, below, which achieve intracellular administration of compounds, such as, for example, liposome administration, may be utilized for the administration of such RNA molecules. The RNA molecules may be produced, for example, by recombinant techniques as is known in the art.

Further, patients may be treated by gene replacement therapy. One or more copies of a normal target gene, or a portion of the gene that directs the production of a normal target gene protein with target gene function, may be inserted into cells using vectors which include, but are not limited to adenovirus, adeno-associated virus, and retrovirus vectors, in addition to other particles that introduce DNA into cells, such as liposomes. Additionally, techniques such as those described above may be utilized for the introduction of normal target gene sequences into human cells.

Cells, preferably, autologous cells, containing normal target gene expressing gene sequences may then be introduced or reintroduced into the patient at positions which allow for the amelioration of symptoms. Such cell replacement techniques may be preferred, for example, when the target gene product is a secreted, extracellular gene product.

Pharmaceutical Preparations and Methods of Administration

The identified compounds that inhibit target gene expression, synthesis and/or activity can be administered to a patient at therapeutically effective doses to treat or ameliorate NPC metastasis. A therapeutically effective dose refers to that amount of the compound sufficient to result in amelioration of symptoms.

Effective Dose

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

BRIEF DESCRIPTION OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein.

Figure 1:
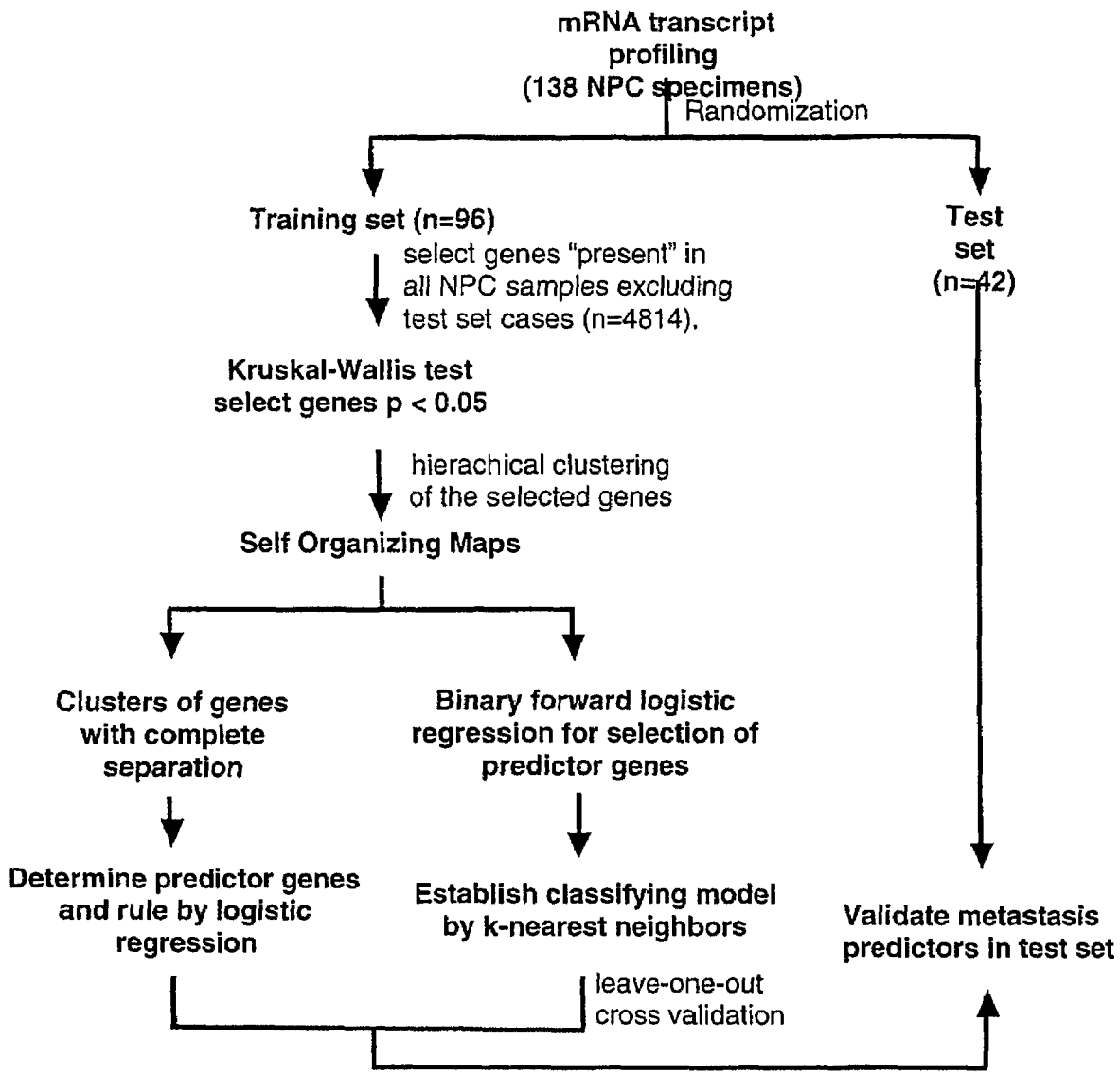
FIG. 1 shows an outline of the strategy used for development and validation of molecular predictors based on mRNA transcript profiling data.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

In preferred aspects, this invention provides:
1. A method of assessing the risk of distant metastasis in a patient having nasopharyngeal carcinoma comprising evaluating the expression profile of at least one of the genes listed in Tables 4 and 5 in a sample from said patient.
2. A method as in 1 comprising evaluating the expression profiles of two or more of the 52 genes listed in Table 4.
3. A method as in 1 comprising evaluating the expression profiles of the 52 genes listed in Table 4.
4. A method as in 3 wherein the evaluation of the expression of the 52 genes listed in Table 4 is performed using a regression model for each of the 9 clusters of genes shown in Table 4.
5. A method as in 4 wherein logit scores are generated for each of the nine gene clusters using the respective regression model equations of Table 1.
6. A method as in 5 wherein a predictive rule for risk of distant metastasis is generated by a k-nearest neighbors classifying method applied to said logit scores for said nine gene clusters.
7. A method as in 1 comprising evaluating the expression profile of two or more of the 12 genes listed in Table 5.
8. A method as in 1 comprising evaluating the expression profiles of the 12 genes listed in Table 5.
9. A method as in 8 wherein the evaluation of the expression of the 12 genes listed in Table 5 is performed using a logistic regression model.
10. A method as in 9 wherein a logit score is generated based on the expression profiles of said 12 genes using the regression model equation of Table 2 and said logit score is correlated with risk of distant metastasis.
11. A method as in 10 wherein predictive rule for low risk of distant metastasis is $$[\text{Probability for low risk of distant metastasis}] = \frac{1}{1 + e^{-(logit\ score)}}.$$

12. A method as in 6 wherein the risk of distant metastasis resulting from said predictive rule is compared with the risk of distant metastasis from a second independent predictive rule which evaluates said risk using the equation $$[\text{Probability for low risk of distant metastasis}] = \frac{1}{1 + e^{-(logit\ score)}}$$

wherein logit score is generated using the regression model equation of Table 2 and the expression profiles of the 12 genes listed in Table 5.

13. A method as in 12 wherein when the risk of distant metastasis determined from both of said methods is low or high, then the risk is scored as low or high, respectively, and when said determined risks are discordant, then the risk is scored as indeterminate.

14. A method as in 1 wherein said expression profile is evaluated in an NPC tumor specimen.

15. A method as in 1 wherein said expression profile is generated from mRNA transcripts.

16. A nucleic acid microarray useful for determining the risk of distant metastasis in a patient having nasopharyngeal carcinoma consisting essentially of probes for determining the expression profiles of (a) the 52 genes listed in Table 4, (b) the 12 genes listed in Table 5, or (c) both said 52 and said 12 genes.

17. A collection in media or kit form consisting essentially of all 52 genes listed in Table 4 and/or all 12 genes listed in Table 5; and/or a subset of said 52 genes or of said 12 genes or both subsets, in each case said subset being effective for predicting risk of distant metastasis in nasopharyngeal carcinoma patients.

EXAMPLES

Example I mRNA transcript profiling was performed on 138 biopsy specimens of primary NPC obtained before therapy. The specimens represented two opposite clinical groups of NPC patients: distant metastasis within three years after initial treatment (high risk group, n=47) versus no distant metastasis after greater than three years follow-up (low risk group, n=91). Two thirds of 138 specimens were randomized to the training set and one third to the test set. Supervised analyses were conducted to discover gene expression signatures associated with development of distant metastasis in the training set (n=96). The discovered molecular predictors were validated in an independent test set of 42 specimens.

Patient Selection and Tumor Tissues

Freshly frozen biopsy samples from primary tumor of 375 NPC patients collected between 1992 and 2004 at the Tumor Bank of the Koo Foundation Sun Yat-Sen Cancer Center (KF-SYSCC) were available for total RNA extraction. Written informed consents were obtained from all patients and the study was approved by the institutional review board. RNAs of 105 patients were seriously degraded and rejected from the study. In the remaining 270 samples, only 138 samples met either of the following criteria and were selected for the study. The first selection criterion called for patients who had not developed distant metastasis and had been regularly followed up for three years or more from the initial treatment. This group of patients (n=91) was designated as clinically low risk for distant metastasis. The second selection criterion called for patients who either had already developed distant metastasis at the time they received the first treatment or developed distant disease within three years from the initial treatment. Distant metastases were defined as metastases of NPC in lungs, bone, liver, kidneys, brain, and other visceral organs. Metastases were confirmed histologically with fine needle aspiration or core biopsy. This group of patients (n=47) was designated as clinically high risk for distant metastasis.

The biopsy samples of primary tumors from all eligible patients were collected between 1995 and 2004, except that one sample was collected in 1992. The majority of the samples (83%) were collected between 1998 and 2001. Ages of patients at the time of diagnosis ranged from 11 to 71 years old with a median and a mean of 44 and 45 years, respectively. After initial diagnoses and staging work-up, patients were treated according to the institutional protocols[31]. The median and the mean durations of follow-up were 3.34 and 3.29 years, respectively. During the follow-up period, 29 patients died and 28 of them were in the clinically high risk group. Staging of NPC patients was conducted according to the 1997 AJCC definition.

mRNA Transcript Profiling Study

Total RNA was isolated from tissues frozen in liquid nitrogen using Trizol reagents (Invitrogen, Carlsbad, Calif.) according to the manufacturer's instruction. The isolated RNA was further purified using RNAEasy Mini kit (Qiagen, Valencia, Calif.), and the quality was assessed by the RNA 6000 Nano assay in an Agilent 2100 Bioanalyzer (Agilent Technologies, Waldbronn, Germany). All RNA samples used for gene expression profiling study had an RNA Integrity Number (RIN) between 6.0 and 10.0 (7.8±1.1, mean ±SD). Hybridization targets were prepared from total RNA according to Affymetrix protocols and hybridized to Affymetrix U133A GeneChips. The U133A GeneChip contained 22,238 probe sets for approximately 13,000 human genes. The characteristics of the array are conventional and, e.g., detailed on the Affymetrix web site (www.affymetrix.com/products/arrays). Briefly, double stranded cDNA was synthesized from 8 μg of total RNA per sample. Biotin-labeled complementary RNA (cRNA) was generated by in vitro transcription from cDNA. The cRNA was purified and chemically fragmented before hybridization. A cocktail was prepared by combining the specific amounts of fragmented cRNA, probe array controls, bovine serum albumin, and herring sperm DNA according to the protocol of the manufacturer. The cRNA cocktail was hybridized to oligonucleotide probes on the U133A GeneChip for 16 hours at 45° C. Immediately following hybridization, the hybridized probe array underwent an automated washing and staining in an Affymetrix GeneChip fluidics station 400 using the protocol EukGE WS2v4. Thereafter, U133A GeneChips were scanned in an Affymetrix GeneArray scanner 2500.

Scaling and Normalization of Microarray Data

The expression intensity of each gene was determined by scaling to a target trimmed-mean of 500 using the Affymetrix Microarray Analysis Suite (MAS) 5.0 software. The scaled expression intensities of all human genes on a U133A GeneChip were logarithmically transformed on base 2, and normalized using the method of quantile normalization.[32] The reference standard for quantile normalization was previously established in our laboratory from U133A GeneChip data of 164 primary NPC, 15 normal nasopharyngeal tissues and 23 metastatic NPC. See U.S. Ser. No. 11/015,764 of Dec. 20, 2004 and 11/090,294 of Mar. 28, 2004, the entire contents of each of which are incorporated by reference herein. Other additional quality measures of U133A GeneChip data include the percentage of genes that were detectible as "present" (52.1±5.8%, mean ±SD), and the ratio of GAPDH 3' to 5'

(0.96±0.18, mean ±SD). Both parameters supported good overall quality of the samples and assays.

Example II

Statistical Analysis of Data

The process of statistical analyses employed is summarized and depicted in FIG. 1.

Division of Samples into Training and Test Sets.

In 138 NPC cases included in our study, 91 cases did not develop any distant metastasis after initiation of the first treatment and were followed for more than three years. These 91 cases were classified as clinically low risk for distant metastasis. In the remaining 47 cases, all developed distant metastasis at the time of the first treatment or within three years after initiation of the first treatment. They were classified as clinically high risk for distant metastasis. The average interval between the first diagnosis date and the first treatment date for all patients was 20±51 days (mean ±SD). Two thirds of patients of each risk group were assigned randomly using SAS software (version 9.1) to the training set. (SAS software is available from SAS Institute Inc., Cary, N.C.) A third of patients was assigned to the test set. Assignment of low risk patients was stratified according to gender, age ($\leq$ and >45 years), 1997 AJCC TNM stage (I and II vs. III and IV), and follow-up duration ($\leq$ and >4.5 years). High risk patients were stratified according to gender, age, TNM stage, and time from the first treatment to the development of distant metastasis ($\leq$ and >1.5 years). There were 62 low risk and 34 high risk cases in the training set; and there were 29 low risk and 13 high risk cases in the independent test set. The independent test set samples were not involved throughout the training process.

Selection of Genes for Analysis

Only probe sets with their expression determined as "present" by Affymetrix MAS5.0 software in all NPC samples excluding the test set samples were selected for analyses. The normalized and logarithmically transformed expression data of each gene was first analyzed by Kruskal-Wallis test between the low and the high risk groups using GeneLinker Platinum 4.5 software (Predictive Patterns Software, Inc., Inverary, Canada). Seven hundred and ninety eight genes with p values <0.05 were selected for further study by the self-organizing maps (SOM) method (GeneLinker Platinum 4.5 software).

SOM Analysis

Figure 2:
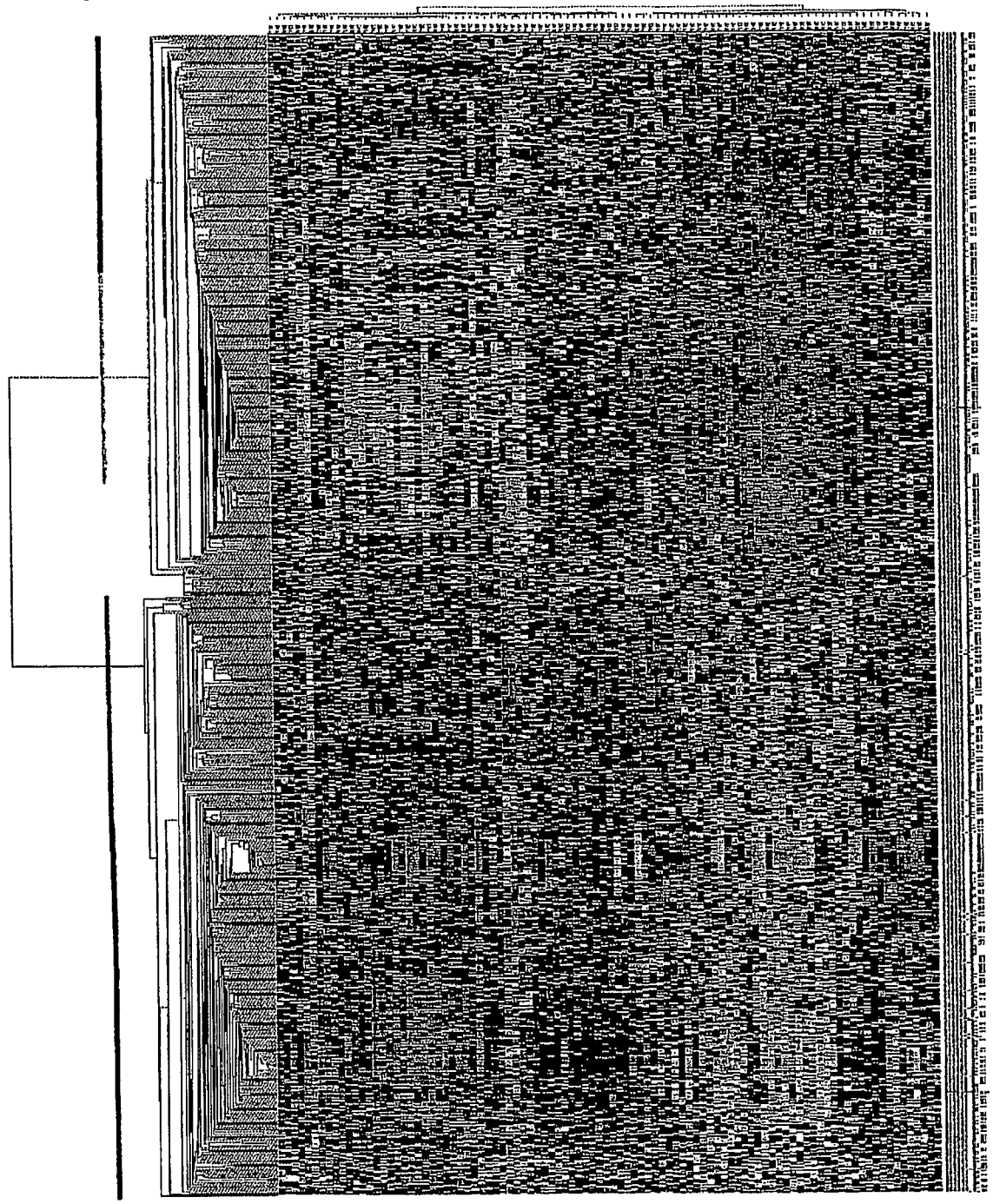
FIG. 2 depicts a hierarchical cluster analysis using 798 genes selected from 96 training set cases. Individual genes are shown in rows as indicated on left and right. Individual cases are shown as columns on top. The results indicate that genes were clustered in 6 groups as indicated by the colored bars on left.

The 798 genes were analyzed by SOM. The parameters set for SOM analysis included orientation by genes, Pearson correlation for distance metric, and map dimension of 2 (height)×3 (width). For reference vector and algorithm properties, the default values were used. The choice of 2×3 dimension was guided by hierachical clustering of 798 genes on the training set cases (FIG. 2). This approach offered an objective means to select a map dimension for SOM analysis. All 798 genes were therefore grouped into six different SOM clusters (I to VI).

Genes in each SOM cluster were further selected by binary forward logistic regression using SPSS 9.0 software (SPSS, Inc., Chicago, Ill.). Entry and removal p values for forward logistic regression were <0.05 and >0.1, respectively. After logistic regression analysis, the numbers of the genes selected from SOM clusters II, V and VI were 6, 6 and 5, respectively. Complete separation was encountered for SOM clusters I, III and IV during logistic regression analysis. Subsequently, two dimensional SOM analysis was performed on genes of SOM clusters I, III and IV, separately. The resulting numbers of the selected genes in the SOM clusters Ia, Ib, IIIa, IIb, IVa, and IVb were 9, 5, 8, 4, 6 and 3, respectively. Thus, there were 52 genes in nine SOM clusters.

Establishment of Predictive Methods

Two predictive methods for identification of NPC patients with high risk of developing distant metastases were established. The first method was based on 52 genes in nine SOM clusters. A regression model was established for the genes of each cluster. The equation of each regression model is listed in Table 1. A logit score was generated from each equation for every sample. The nine logit scores for each sample in the training set were used to develop the predictive rule by the k-nearest neighbors (k-NN) classifying method using SAS 9.0 software. "k" values of 1, 3, 5, 10 and 30 were separately tested by using the training set. Leave-one-out cross-validation was conducted. The tested k value of 10 gave the best result according to leave-one-out cross-validation and was chosen for the predictive method.

The second predictive method was based on 12 genes derived from 197 genes in the original SOM cluster I. As mentioned above, three SOM clusters of genes showed complete separation during logistic regression with forward selection analysis. The results suggested potential high predictive value of genes of these three SOM clusters. In order to identify genes of which SOM cluster could be reliably used for prediction, gene selection was conducted from each SOM cluster by binary forward logistic regression (SPSS 9.0 software) using the training set cases and the selection of genes was stopped right before encountering complete separation. The selected genes from each cluster were used to derive a logit score which was used to estimate the probability. Probability greater than 0.5 was assigned to low risk for distant metastasis, and probability less than 0.5 was assigned to high risk for distant metastasis. The results showed that 12 genes selected from the SOM cluster I produced the best results using the cases in the training set. The equation of the regression model based on the 12 genes from the SOM cluster I is shown in Table 2.

Survival Analysis

Metastasis-free and overall survival analyses were carried out by Kaplan-Meier log rank test using SAS 9.0 software. Survival was defined as the duration between the beginning date of the first treatment and the last follow-up date or the date of death. Metastasis-free survival was defined as the duration between the beginning date of the first treatment and the date of the first distant metastasis diagnosed.

Example III

Results Summary

As shown, two predictors were established for identification of NPC patients at high or low risk of developing distant metastasis. The first predictor was based on 52 genes in nine different self organizing maps clusters and a k-nearest neighbors classifying method. The second predictor was based on 12 genes and a logistic regression model. Both methods were strongly predictive for short interval to distant metastasis and short overall survival in the independent test set. The overall accuracies of both methods assessed in the independent test set cases were 81% and 76%, respectively. When both predictive methods were combined, the accuracy was increased to 85%. The estimated hazard ratio for distant metastasis in the group of high risk signature, as compared with the group of low risk signature, was 11.1 (95% confidence interval 2.4 to 52.4, p=0.002).

Characteristics of the Patients

To identify gene signatures for prediction of NPC patients at high or low risk of developing distant metastasis with poor or good overall survival, a supervised analysis was conducted between two groups of clinically well defined NPC patients. It is well recognized that NPC patients who did not develop distant metastasis within three years after the initial treatment had good long term metastasis-free and overall survival.[31,33] By contrast, NPC patients who developed distant metastasis, at the time of or within three years after the first treatment, usually died of the disease and had poorer survival. Among 138 patients in our study, 91 patients belonged to the clinically low risk group and 47 patients to the clinically high risk group. Two thirds of the low and the high risk patients were randomly assigned to the training set and one third to the test set. The characteristics of these patients are summarized in Table 3. There were no significant differences for the listed clinical characteristics between the training set and the test set cases for both low and high risk groups. In addition, the distribution of distant metastatic sites between the training set (n=34) and the test set (n=13) for bone was 50% vs 69%, liver 50% vs 54%, lungs 38% vs 23%, others 15% vs 23%. Others included brain, kidneys, spleen and pelvis organs. The distribution was similar between the two groups.

Example IV

Prediction of Distant Metastasis by Signature of 52 Genes

To identify predictor genes, a highly supervised analysis was conducted. Only genes (4,814 probe sets) that could be determined as "present" by Affymetrix MAS 5.0 software in all NPC samples excluding the test set cases were used for the study. We then performed a Kruskal-Wallis test between the clinically low and the clinically high risk groups of the training set. Seven hundred and ninety eight genes showing significant difference ($p<0.05$) with their expression were selected for further study. An unsupervised hierachical cluster analysis was performed on the training set cases using the 798 chosen genes. The results showed six major gene clusters (FIG. 2). On the basis of the hierachical clustering result, a map dimension of 2×3 was chosen for SOM analysis. Most genes in each SOM cluster aggregated together and were in parallel with the gene clusters generated by hierachical clustering.

The genes in each of the six SOM clusters were further analyzed by logistic regression with forward selection for the low and the high risk cases in the training set. Three SOM clusters of genes showed the problem of complete separation. The genes in each of these three clusters were further analyzed by SOM for two sub-clusters. A total of 52 genes were selected from nine SOM clusters and used to develop a predictive model for distant metastasis. These 52 genes are summarized in Table 4. The equations used to determine the logit score from genes in each SOM cluster are summarized in Table 1.

Thus, nine logit scores were generated from the expression intensities of the 52 genes for each case. The nine logit scores of each case in the training set were used to establish a predictive rule by k-NN classifying method. Leave-one-out cross validation for the predictive rule showed that the specificity and the sensitivity for prediction of training set cases with high risk of distant metastasis were 98% (61/62) and 88% (30/34), respectively. The overall accuracy was 95% (91/96). When the independent test set cases (n=42) were analyzed according to the established predictive rule; the specificity, the sensitivity and the overall accuracy were 86% (25/29), 69% (9/13), and 81% (34/42), respectively. Fisher's exact test for association (p=0.0007) confirmed the robustness of the 52-genes predictor. The estimated hazard ratios between the predicted high risk and the predicted low risk signature groups for distant metastasis and shorter overall survival were 7.1 (p=0.002, 95% confidence interval 2.2-23.5) and 5.4 (p=0.001, 95% confidence interval 1.5-19.4), respectively.

Figure 3:
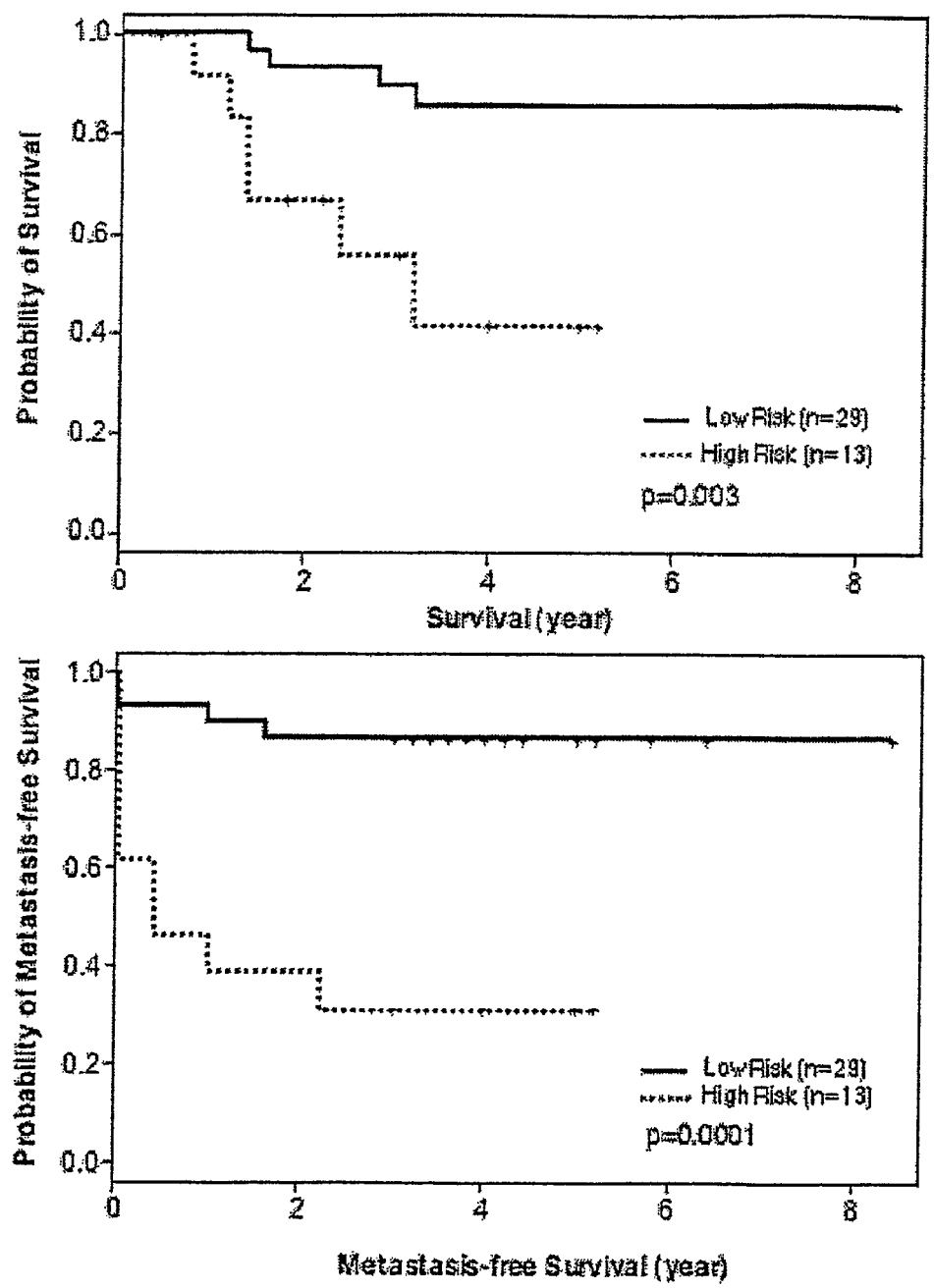
FIG. 3 shows Kaplan-Meier analyses of probabilities of metastasis-free and overall survival for cases predicted low and high risk for distant metastasis by 52-genes signature and k-nearest neighbors classifying method. The results shown were obtained from the independent test set cases. The p values were calculated with log-rank test.

When the patients in the test set predicted as low (n=29) or high (n=13) risk for distant metastasis were compared for their metastasis-free and overall survival, patients predicted as having high risk for distant metastasis had significantly shorter metastasis free survival (p=0.0001) and shorter overall survival (p=0.003) (FIG. 3).

Example V

Prediction of Distant Metastasis by Signature of 12 Genes

The second predictive method was based on 12 genes selected by logistic regression analysis from genes in the SOM cluster I. The equations used to calculate the probability of low risk for distant metastasis are summarized in Table 2. The 12 genes are listed in Table 5. When the 12-genes predictive rule was applied to the independent test set cases (n=42), the sensitivity, the specificity and the overall accuracy for prediction of high metastatic risk were 85% (11/13), 72% (21/29) and 76% (32/42), respectively. For the 12-genes predictor, Fisher's exact test for association (p=0.0008) confirmed similar robustness like the 52-gene predictor. The estimated hazard ratios between the predicted high risk and the predicted low risk signature groups for distant metastasis and shorter overall survival were 8.2 (p=0.006, 95% confidence interval 1.8-37.4) and 6.3 (p=0.02, 95% confidence interval 1.3-29.7), respectively.

Figure 4:
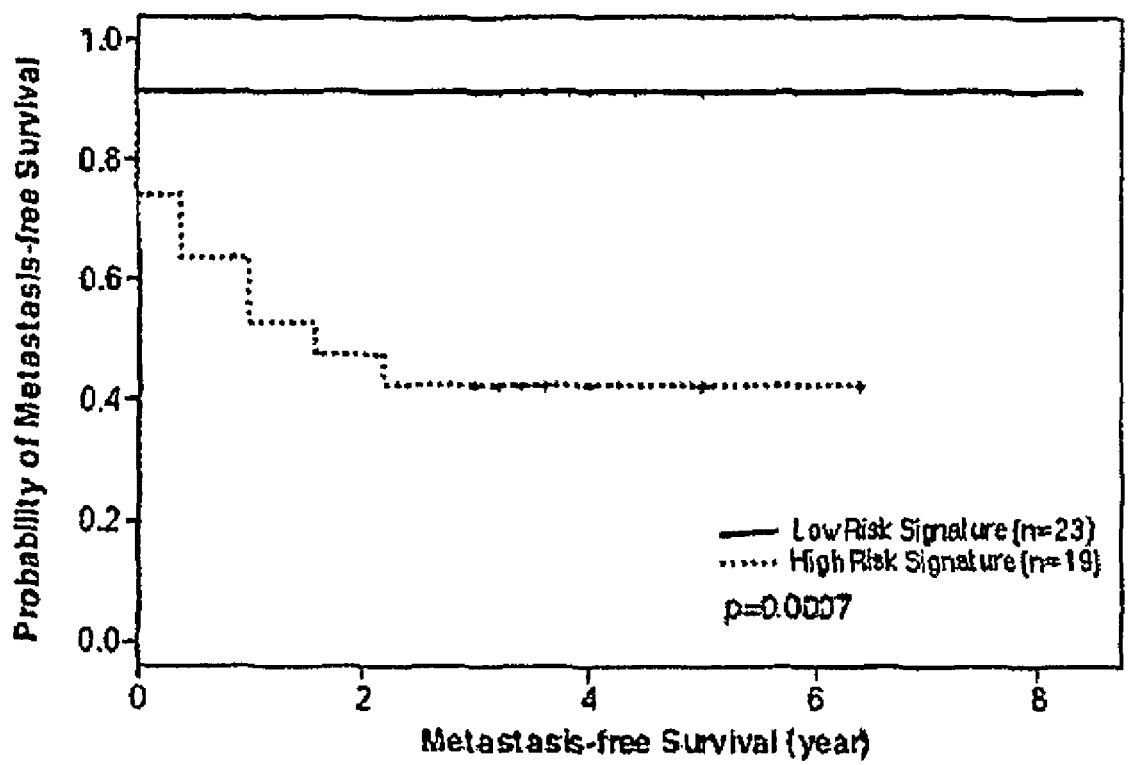
FIG. 4 shows Kaplan-Meier analyses of probabilities of metastasis-free and overall survival for cases predicted low and high risk for distant metastasis by 12-genes signature and the logistic regression model. The results shown were obtained from the independent test set cases. The p values were calculated with log-rank test.
Figure 4:
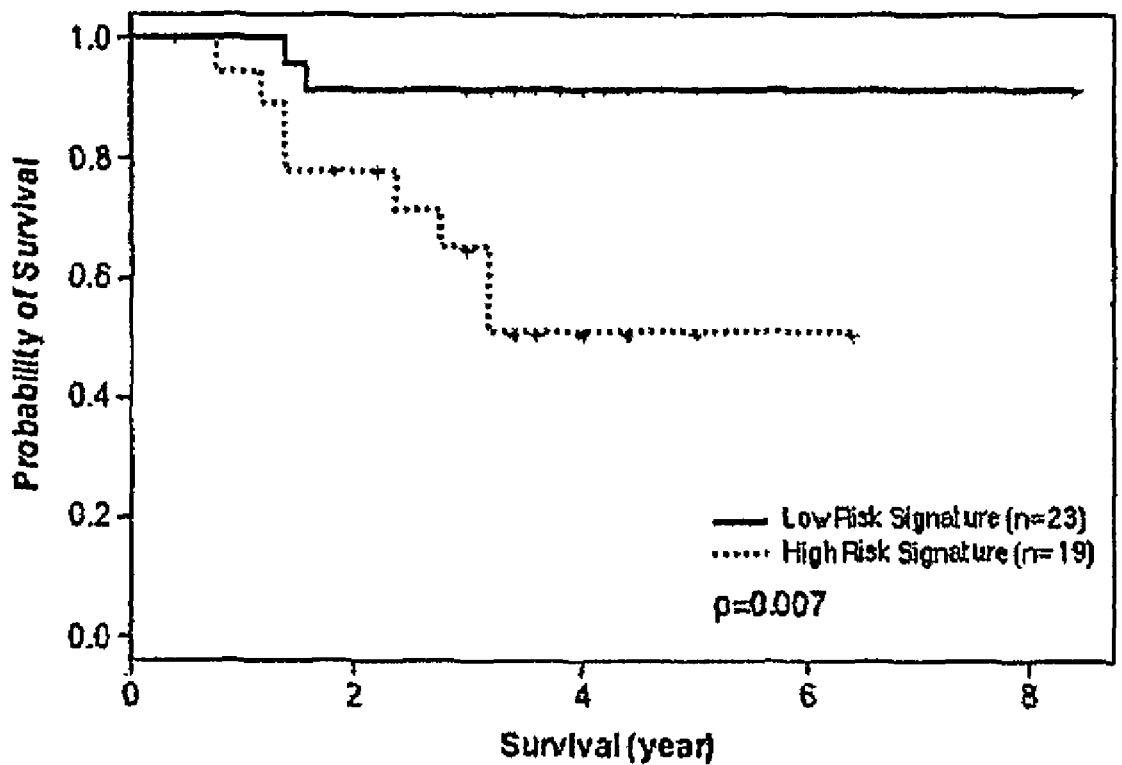

When cases predicted as low risk (n=23) or high risk (n=19) by the 12-genes predictor were analyzed for the metastasis-free and the overall survival, the results showed significantly shorter metastasis-free (p=0.0007) and overall (p=0.007) survival for patients predicted as having high risk for distant metastasis (FIG. 4).

Example VI

Prediction of Distant Metastasis by Combined Signatures

Figure 5:
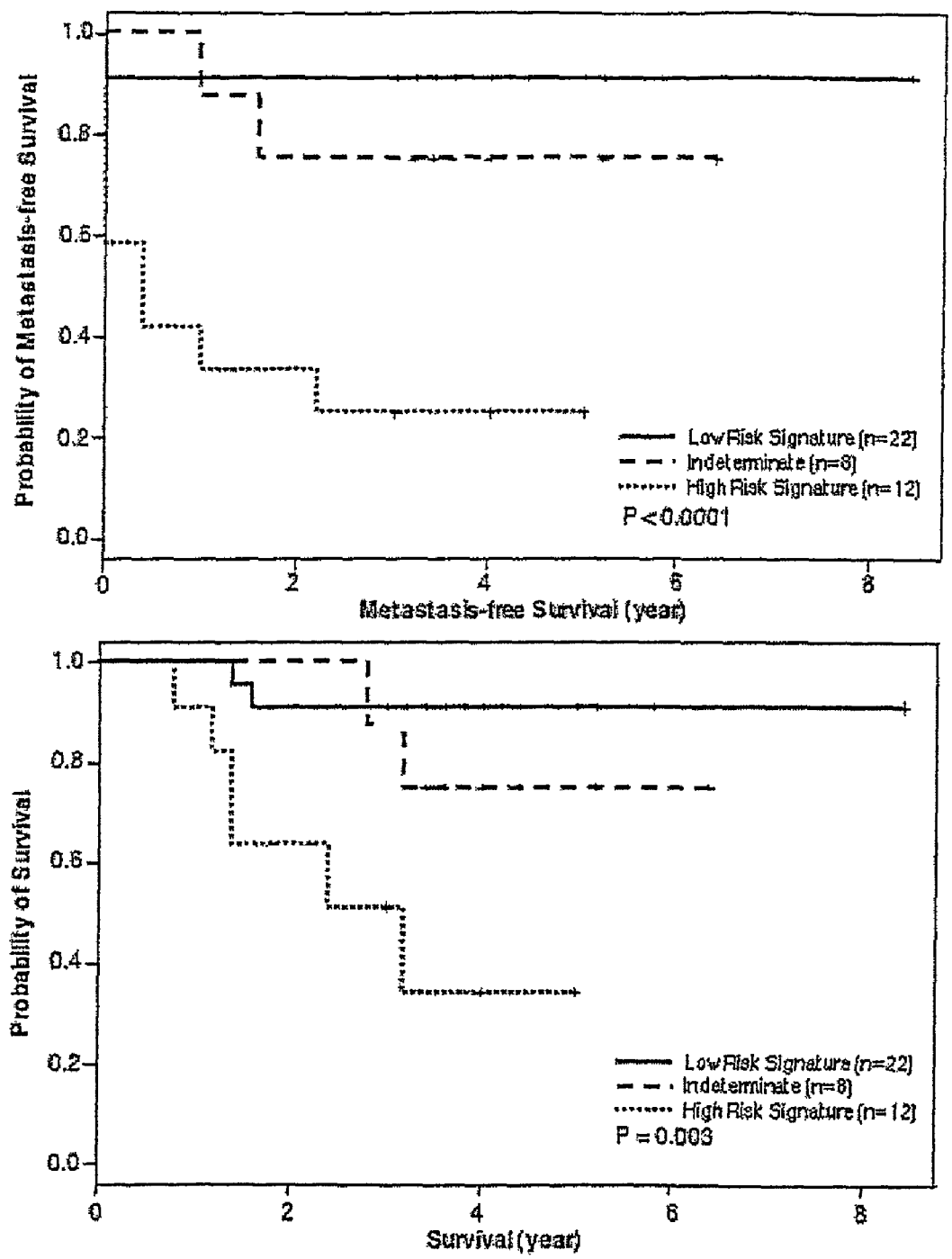
FIG. 5 shows Kaplan-Meier analyses of probabilities of metastasis-free and overall survival according to the combined predictive results of 52-genes and 12-genes signatures. The cases showing discordant results between two signatures were regarded as "indeterminate" (Table 6). The cases showing concordant results fell into either low or high risk for distant metastasis. When the groups of low and high risk signature were compared for metastasis-free and overall survival, p values were <0.0001 and 0.002, respectively. There were no significant differences between the indeterminate group and the low or the high risk group for metastasis-free survival (p=0.09 and 0.05) and overall survival (p=0.31 and 0.09). The p values were calculated with the use of log-rank test.

When the results of the two predictive methods of Example IV and V were analyzed for their concordance in the independent test set cases, 22 cases (52%) were predicted low risk and 12 cases (29%) were high risk by both methods (Table 6). Eight cases (19%) were discordant between two methods and regarded as indeterminate. Among the concordant cases (n=34), five were incorrectly predicted. Three cases were false positive and two were false negative. Thus, the overall accuracy was 85% (29/34). The estimated hazard ratios between the high risk and the low risk signature groups for distant metastasis and shorter overall survival were 11.1 (p=0.002, 95% confidence interval 2.4-52.4) and 8.5 (p=0.009, 95% confidence interval 1.7-42.8), respectively. Survival analyses of the cases predicted as low risk, high risk and indeterminate revealed that high risk cases had significantly worse metastasis-free and overall survival than those predicted as low risk (FIG. 5). The difference of metastasis-free and overall survival between the low risk and the indeterminate cases were not statistically significant.

Example VII

Comparison of Survival Between Stage III and IV NPC Patients

Figure 6:
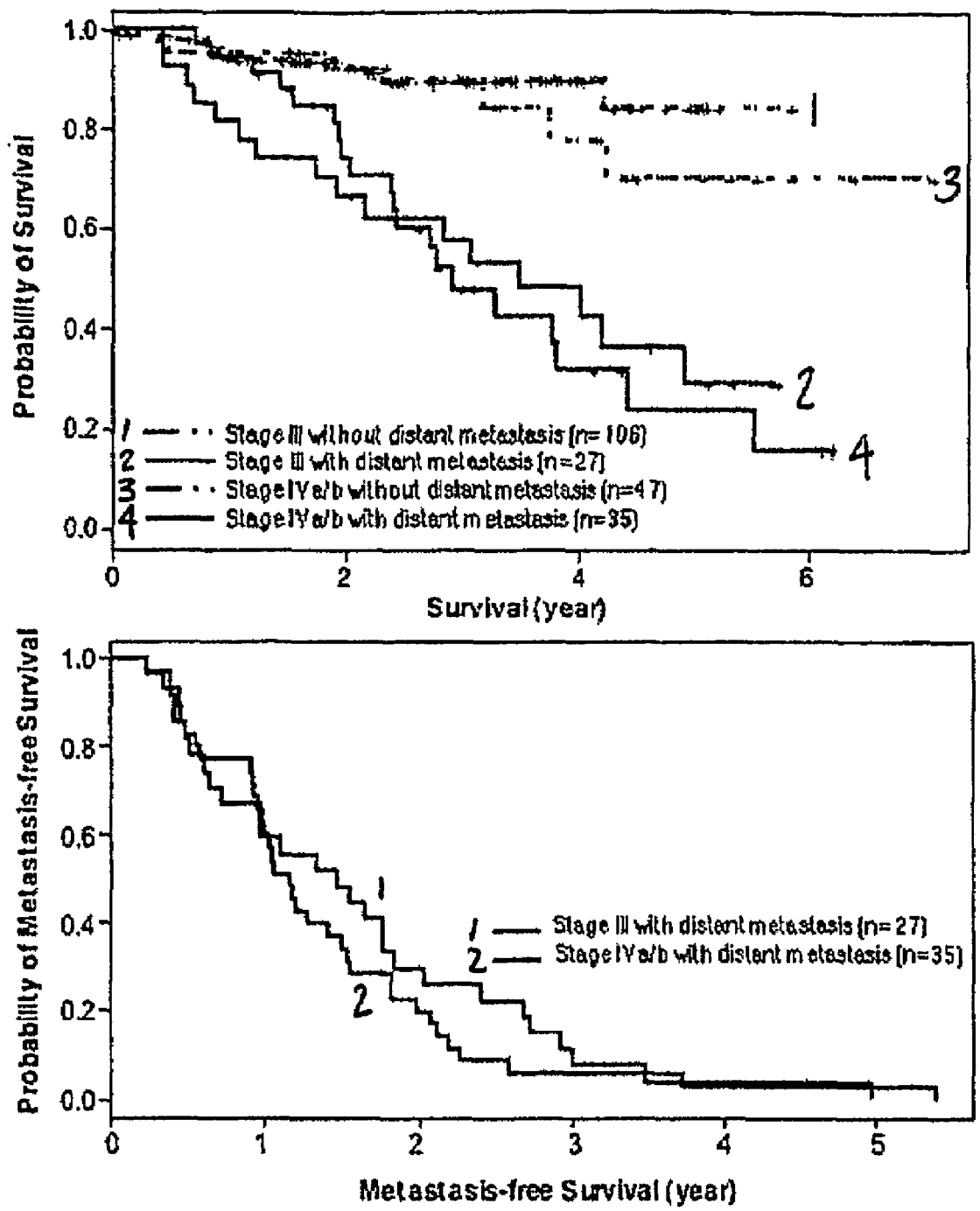
FIG. 6 shows Kaplan-Meier analyses of probabilities of overall and metastasis-free survival between stage III or IVa/b NPC patients with and without distant metastases. Most patients included in the study began to receive their treatment between 1997 and 2002 according to the institutional protocols and were followed regularly. Upper panel shows the overall survival curves of these four groups of patients. There were 106 and 27 stage III patients without and with development of distant metastases, respectively. Similarly, there were 47 and 35 stage 1V patients. The differences of overall survival between patients with and without development of distant metastases for stage III or IVa/b patients were significant with both p values <0.0001. There were no significant differences between stage III and IVa/b patients with (p=0.39) or without (p=0.35) distant metastasis. Lower panel shows probabilities of metastasis-free survival for stage III and IVa/b patients who eventually developed distant metastases. All stage III patients were treated with concurrent chemo-radiation therapy and adjuvant chemotherapy only, whereas maintenance chemotherapy was added for stage IVa/b patients.
Figure 7:
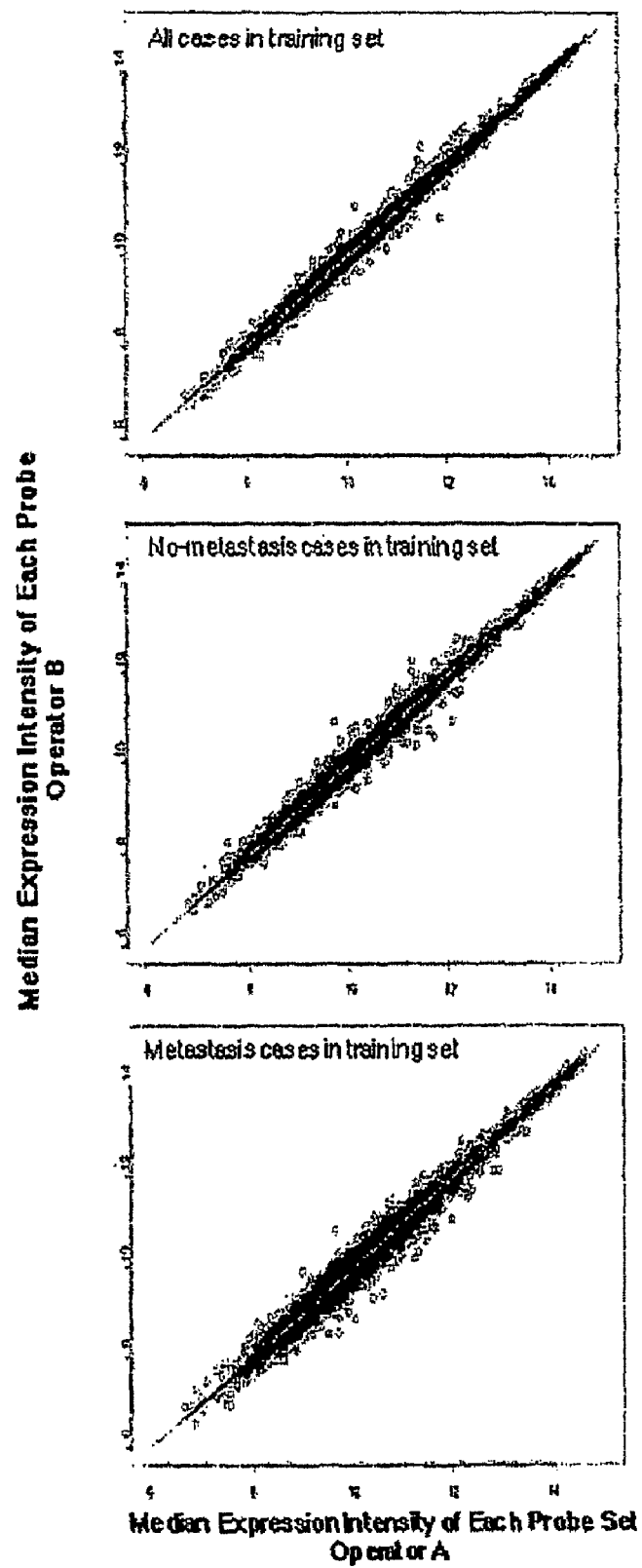
FIG. 7 shows correlation of median intensities of "present" probe sets between two different operators. All NPC specimens in the training sets were randomly performed by two operators. Operator A performed 24 no-metastasis cases and 14 positive metastasis cases in the training set. Operator B performed 35 no-metastasis and 18 positive metastasis cases. The median of the normalized expression intensities for each probe set of the cases performed by each operator was calculated. The results showed perfect diagonal linear correlation indicating that there was no systematic bias associated with operators.
Figure 8:
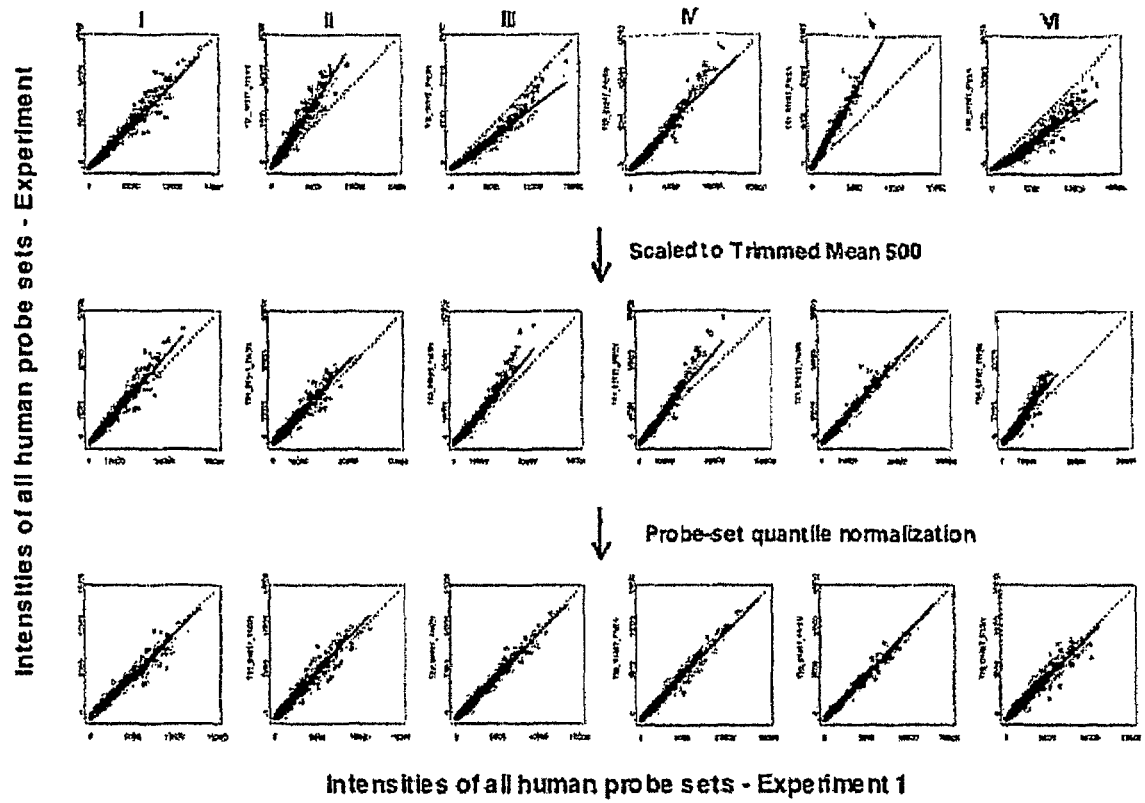
FIG. 8 shows the results of Quantile normalization at probe set level for correction of experimental variations. cRNA samples from six different NPC specimens (I-VI) were divided into two portions and hybridized to two U133-A GeneChips on different dates. The correlation of intensities of all probe sets for human genes on U133-A GeneChip was performed for each case as shown in the figure. Upper panel shows correlation of probe set intensities from chip file without normalization. Middle panel shows correlation of probe set intensities after scaling to a trimmed mean of 500. Lower panel shows correlation of probe set intensities after quantile normalization of expression intensities of all human probe sets to a previously established standard. The results show that quantile normalization at probe set level is effective to correct experimental variations.

In order to learn the potential clinical impact of the established predictive methods, clinical data of 133 stage III and 82 stage IVa and IVb (IVa/b) NPC patients were collected. Among these patients, only 90 were part of the above mRNA transcript profiling study. All patients had been treated and regularly followed up according to institutional protocols[31] between 1997 and 2003. The patients of TNM stage III or IVa/b were further divided into two groups according to the subsequent development of distant metastases. The overall and the metastasis-free survivals of these four groups of patients were compared. The results showed that NPC patients with stage III disease who subsequently developed distant metastases had overall and metastasis-free survival similar to patients with stage IVa/b diseases who also developed distant metastasis (n=35) (FIG. 6). In contrast, stage III (n=106) or IVa/b (n=47) patients without development of distant metastases had much better overall survival than those patients with distant metastasis (FIG. 6).

The results indicated that there were two diverse groups in stage III or IVa/b patients. One group had low risk of developing distant metastasis and good clinical outcome. The other developed distant metastasis within three years after the initial treatment and had poor survival outcome (FIG. 6). These findings support that accurate prediction of patients who are at high risk of developing distant metastases not only has important prognostic implication, but also provides a means to select appropriate patients for testing new therapeutic modalities to improve long term treatment outcome.

REFERENCES

1. Lo, W. K., To, K. F. & Huang, D. P. Focus on nasopharyngeal carcinoma. Cancer Cell 5, 423-428 (2004).
2. Altun, M. et al. Undifferentiated nasopharyngeal cancer (UCNT): current diagnostic and therapeutic aspects. Int. J. Radiat. Oncol. Biol. Phys. 32:859-877 (1995).
3. Young, L. S. & Riskinson, A. B. Epsein-Barr virus: 40 years on. Nature Rev Cancer 4:757-768 (2004).
4. Cohen, J. I. Epstein-Barr virus infection. New Eng J Med 343, 481-492 (2000).
5. Yu, M. C. Nasopharyngeal carcinoma: Epidemiology and Dietary Factors pp. 39-47. Lyon:IARC, (1991)
6. Ho, J. Nasopharyngel carcinoma. Adv. Cancer Res. 15:59-72 (1972)
7. Yeh, S. & Cowdry, E. Incidence of malignant tumors in Chinese. Cancer 7:425-436, 1954.
8. Yu, M. C. & Henderson, B. E. Nasopharyngeal cancer. In: Schottenfield D, Fraumeni J F, eds. Cancer epidemiology and prevention. 2$^{nd}$ ed. New York: Oxford Univ. Press 1996: 603-18.
9. Fandi, A. et al. Nasopharyngeal cancer: epidemiology, staging, and treatment. Semin. Oncol. 21:382-397 (1994).
10. Vikram, B, et al. Patterns of failure in carcinoma of the nasopharynx: failure at distant sites. Head Neck Surg. 8:276-279 (1986).
11. Hung, S. C. Nasopharyngeal cancer: a review of 1605 paatients treated radically with cobalt 60. Int. J. Radiat. Oncol. Biol. Phys. 6:401-407 (1980).
12. Geara, F. B. et al. Carcinoma of the nasopharynx treated by radiotherapy alone: determinants of distant metastasis and survival. Radiother. Oncol. 43:53-61 (1997).
13. Perez, C. A. et al. Carcinoma of the nasopharynx; factors affecting prognosis. Int. J. Radiat. Oncol. Biol. Phys. 23:271-280 (1992).
14. Lee, A. W. M. et al. Retrospective analysis of 5037 patients with nasopharyngeal carcinoma treated during 1976-1985: overall survival and patterns of failure. Int. J. Radiat. Oncol. Biol. Phys. 23:261-270 (1992).
15. Agulnik, M. & Siu, L. L. State-of-the-art management of nasopharyngeal carcinoma: current and future directions. Br. J. Cancer 92:799-806 (2005).
16. Langendijk J A, Leemans C R, Buter J, et a;/ The additional value of chemotherapy to radiotherapy in locally advanced nasopharyngeal carcinoma: a meta-analysis of he published literature. J Clin Oncol 2004; 22:4604-4612.
17. Chang, J. T-C. et al. Nasopharyngeal carcinoma staging by 9180F-fluorodeoxyglucose positron emission tomography. Int. J. Radiat. Oncol. Biol. Phys. 62:501-507 (2005).
18. Perou, C. M. et al. Molecular portraits of human breast tumours. Nature 406:747-752 (2000).
19. Alizadeh A A, Eisen M B, Davis R E, et al. Distinct types of diffuse large B-cell lymphoma identified by gene expression profiling. Nature 2001; 405:503-511.
20. Khan J, Wei J S, Ringer M, et al. Classification and diagnostic prediction of cancers using gene expression profiling and artificial neural networks. Nature Med 2001; 7; 673-679.
21. Dyrskjot L, Thykjaer T, Kruhoffer M, et al. Identifying distinct classes of bladder carcinoma using microarrays. Nature Gent 2003; 33:90-96.
22. Bullinger L, Dohner K, Blair e, et al. Use of gene-expression profiling to identify prognostic subclasses in adult acute myeloid leukemia. New Eng J Med 2004; 350:1605-1615.
23. van't Veer L J, Dai H, van de Vijver M J, et al: Gene expression profiling predicts clinical outcome of breast cancer. Nature 2002; 415:530-536.
24. Pomeroy S L, Tamayo P, Gaasenbeek M, et al. Prediction of central nervous system embryonal tumour outcome based on gene expression. Nature 2002; 415:436-442.
25. Shipp M A, Ross K N, Tamayo P, et al. Diffuse large B-cell lymphoma outcome prediction by gene-expression profiling and supervised machine learning. Nature Med 2002; 8:68-74.
26. Rosenwald A, Wright G, Chan W C, et al. The use of molecular profiling to predict survival after chemotherapy for diffuse large B-cell lymphoma. New Eng J Med 2002; 346:1937-1947.
27. Huang E, Cheng S H, Dressman H, et al. Gene expression predictors of breast cancer outcome. Lancet 2003; 361: 1590-1596.
28. Ayers M, Symmans W F, Stec J, et al. Gene expression profiles predict complete pathologic response to neoadjuvant paclitaxel and fluorouracil, doxorubicin, and cyclophosphamide chemotherapy in breast cancer. J Clin Oncol 2004; 22:2284-2293.
29. Mazzanti C, Zeiger M A, Costourpus N, et al. Using gene expression profiling to differentiate benign versus malignant thyroid tumors. Cancer Res 2004; 64:2898-2903.
30. Roepman P, Wessels L F A, Kettelarij N, et al. An expression profile for diagnosis of lymph node metastasis from primary head and neck squaamous cell carcinoma. Nature Genetics 2005; 37:182-186.
31. Cheng S H, Tsai S Y C, Yen K L, et al. Prognostic significance of parapharyngeal space venous plexus and marrow involvement; potential landmarks of dissemination for stage I-III nasopharyngeal carcinoma. Int J Radiat Oncol Biol Phys 2005; 61:456-465.

32. Bolstad B M, Irizarry R A, Astrand M, et al. A comparison of normalization methods for high density oligonucleotide array data based on variance and bias. Bioinformatics 2003; 19:185-193.
33. Lee A W M, Sze W M, Au J S K, et al. Treatment results for nasopharyngeal carcinoma in the modern era: the hong Kong Experience. Int J. Radiat Oncol Biol Phys 2005; 61:1107-1116.
34. Yokota S, Yamamoto Y, Shimizu K, et al. Increased expression of cytosolic chaperonin CCT in human hepatocellular and colonic carcinoma. Cell Stress Chaperones 2001; 6:345-350.
35. Liu H, Li J & Wong L. Use of extreme patient samples for outcome prediction from gene expression data. Bioinformatics 2005; 21:3377-3384.
36. Simon R, Radmacher M D, Dobbin K, et al. Pitfalls in the use of DNA microarray data for diagnostic and prognostic classification. JNCI-2003; 95:14-18.
37. Chang Y, Lee T C, Li J C, Lai T L, Chua H H, Chen C L, Doong S L, Chou C K, Sheen T S, Tsai C H. Differential expression of osteoblast-specific factor 2 and polymeric immunoglobulin receptor genes in nasopharyngeal carcinoma. Head Neck. 2005 Aug. 31
38. Fang W Y, Liu T F, Xie W B, Yang X Y, Wang S, Ren C P, Deng X, Liu Q Z, Huang Z X, Li X, Ding Y Q, Yao K T. Reexploring the possible roles of some genes associated with nasopharyngeal carcinoma using microarray-based detection. Acta Biochim Biophys Sin (Shanghai). 2005 August; 37(8):541-6.
39. Lung H L, Bangarusamy D K, Xie D, Cheung A K, Cheng Y, Kumaran M K, Miller L, Liu E T, Guan X Y, Sham J S, Fang Y, Li L, Wang N, Protopopov A I, Zabarovsky E R, Tsao S W, Stanbridge E J, Lung M L. THY1 is a candidate tumour suppressor gene with decreased expression in metastatic nasopharyngeal carcinoma. Oncogene. 2005 Jun. 20; [Epub ahead of print]
40. Zhang B, Nie X, Xiao B, Xiang J, Shen S, Gong J, Zhou M, Zhu S, Zhou J, Qian J, Lu H, He X, Li X, Hu G, Li G. Identification of tissue-specific genes in nasopharyngeal epithelial tissue and differentially expressed genes in nasopharyngeal carcinoma by suppression subtractive hybridization and cDNA microarray. Genes Chromosomes Cancer. 2003 September; 38(1):80-90.
41. Guo X, Lui W O, Qian C N, Chen J D, Gray S G, Rhodes D, Haab B, Stanbridge E, Wang H, Hong M H, Min H Q, Larsson C, Teh B T. Identifying cancer-related genes in nasopharyngeal carcinoma cell lines using DNA and mRNA expression profiling analyses. Int J Oncol. 2002 December; 21(6):1197-204.
42. Hui A B, Lo K W, Teo P M, To K F, Huang D P. Genome wide detection of oncogene amplifications in nasopharyngeal carcinoma by array based comparative genomic hybridization. Int J Oncol. 2002 March; 20(3):467-73.
43. Soo R, Putti T, Tao Q, Goh B C, Lee K H, Kwok-Seng L, Tan L, Hsieh W S. Overexpression of cyclooxygenase-2 in nasopharyngeal carcinoma and association with epidermal growth factor receptor expression. Arch Otolaryngol Head Neck Surg. 2005 February; 131(2):147-52
44. Lee S W, Cho K J, Park J H, Kim S Y, Nam S Y, Lee B J, Kim S B, Choi S H, Kim J H, Ahn S D, Shin S S, Choi E K, Yu E. Expressions of Ku70 and DNA-PKcs as prognostic indicators of local control in nasopharyngeal carcinoma. Int J Radiat Oncol Biol Phys. 2005 Aug. 1; 62(5):1451-7.
45. Ma B B, Poon T C, To K F, Zee B, Mo F K, Chan C M, Ho S, Teo P M, Johnson P J, Chan A T. Prognostic significance of tumor angiogenesis, Ki 67, p53 oncoprotein, epidermal growth factor receptor and HER2 receptor protein expression in undifferentiated nasopharyngeal carcinoma—a prospective study. Head Neck. 2003 October; 25(10):864-72.
46. Farias T P, Dias F L, Lima R A, Kligemman J, de Sa G M, Barbosa M M, Goncalves F B Jr. Prognostic factors and outcome for nasopharyngeal carcinoma. Arch Otolaryngol Head Neck Surg. 2003 July; 129(7):794-9.
47. Hsiao J R, Jin Y T, Tsai S T, Shiau A L, Wu C L, Su W C. Constitutive activation of STAT3 and STAT5 is present in the majority of nasopharyngeal carcinoma and correlates with better prognosis. Br J Cancer. 2003 Jul. 21; 89(2):344-9.
48. Chan A T, Lo Y M, Zee B, Chan L Y, Ma B B, Leung S F, Mo F, Lai M, Ho S, Huang D P, Johnson P J. Plasma Epstein-Barr virus DNA and residual disease after radiotherapy for undifferentiated nasopharyngeal carcinoma. J Natl Cancer Inst. 2002 Nov. 6; 94(21):1614-9.
49. Ma J, Nicholas, Terry H A, Lin S X, Patel N, Mai H G, Hong M H, Lu T X, Cui N J, Min H Q. Prognostic significance of DNA ploidy and proliferative indices in patients with nasopharyngeal carcinoma. Ai Zheng. 2002 June; 21(6):644-50.
50. Rubio L, Burgos J S, Lopez-Guerrero J A, Morera C, Vera-Sempere F J. Expression of p53 protein and tumor angiogenesis as prognostic factors in nasopharyngeal carcinoma patients. Pathol Res Pract. 2002; 198(2):97-102.
51. Fujii M, Yamashita T, Ishiguro R, Tashiro M, Kameyama K. Significance of epidermal growth factor receptor and tumor associated tissue eosinophilia in the prognosis of patients with nasopharyngeal carcinoma. Auris Nasus Larynx. 2002 April; 29(2): 175-81.
52. o Y M, Chan A T, Chan L Y, Leung S F, Lam C W, Huang D P, Johnson P J. Molecular prognostication of nasopharyngeal carcinoma by quantitative analysis of circulating Epstein-Barr virus DNA. Cancer Res. 2000 Dec. 15; 60(24):6878-81.
53. Heng D M, Wee J, Fong K W, Lian L G, Sethi V K, Chua E T, Yang T L, Khoo Tan H S, Lee K S, Lee K M, Tan T, Chua E J. Prognostic factors in 677 patients in Singapore with nondisseminated nasopharyngeal carcinoma. Cancer. 1999 Nov. 15; 86(10):1912-20.
54. Guo X, Min H Q, Zeng M S, Qian C N, Huang X M, Shao J Y, Hou J H. nm23-H1 expression in nasopharyngeal carcinoma: correlation with clinical outcome. Int J Cancer. 1998 Dec. 18; 79(6):596-600.

TABLE 1

Equations of logistic regression model for selected genes in nine SOM clusters

LOGIT Ia = (200640_at) × 4.6445 + (200910_at) × (−4.9525) + (202397_at) × 3.6645 + (208114_s_at) × 5.4097 + (208699_x_at) × 2.9153 + (212247_at) × 2.2052 + (213175_s_at) × 3.4262 + (214431_at) × (−3.4637) + (222011_s_at) × 4.4282 − 183.906

LOGIT Ib = (201892_s_at) × 2.0433 + (215157_x_at) × 3.0064 + (217870_s_at) × 2.1101 + (218973_at) × 4.07 + (221494_x_at) × (−3.6926) − 79.0097

LOGIT II = (200976_s_at) × (−3.8876) + (205434_s_at0 × (−1.8483) + (211974_x_at) × (−3.3451) + (213408_s_at) × (−3.8384) +

TABLE 1-continued

Equations of logistic regression model for selected genes in nine SOM clusters (217917_s_a) × (−5.3073) + (221971_x_at) × 7.0464 + 126.459
LOGIT IIIa = (201123_s_at) × 0.8651 + (201642_at) × 3.9114 + (202301_s_at) × 7.9516 + (206544_x_at) × (−1.8805) + (208698_s_at) × 2.8301 + (211115_x_at) × 4.0432 + (211575_s_at) × (−4.3726) + (211913_s_at) × (−2.2606) − 117.98
LOGIT IIIb = (200880_at) × 2.7955 + (208765_s_at) × 2.1072 + (209157_at) × 2.2478 + (212398_at) × 3.4807 − 104.518
LOGIT IVa = (201178_at) × (−2.6194) + (212911_at) × (−2.4526) + (213254_at) × (−1.7758) + (217969_at) × 2.475 + (218659_at) × 3.3188 + (64418_at) × (−2.4296) + 22.4303
LOGIT IVb = (202211_at) × (−2.1207) + (212884_x_at) × (−1.0461) + (221269_s_at) × (−0.9598) + 40.9722
LOGIT V = (200921_s_at) × (−2.6385) + (201057_s_at) × (−2.5845) + (207335_x_at) × (−2.7044) + (209584_x_at) × (−1.6973) + (211733_x_at) × (−4.2067) + (217118_s_at) × (−2.539) + 171.7096
LOGIT VI = (201266_at) × 2.5851 + (202905_x_at) × 2.7306 + (203006_at) × 1.6767 + (206559_x_at) × 13.1357 + (212295_s_at) × 2.7269 − 286.114

Affymetrix probe set identification numbers in parentheses represent the normalized expression intensity of the mRNA transcript for the indicated probe sets. Logit scores were calculated from the listed equations and used to predict metastasis risk by k-nearest neighbors method

TABLE 2

Equation for calculation of logit score based on the expression intensities of 12 genes to estimate risk of distant metastasis Equation for logistic regression model to calculate logit score:

$\log it(\pi)$ = 459.9 + (200057_s_at) × (−12.5305) + (200842_s_at) × 12.3230 + (200910_at) × 21.4064 + (201892_s_at) × (−10.5046) + (201947_s_at) × 20.0446 + (201948_at) × (−17.7163) + (208114_s_at) × (−35.1981) + (208699_x_at) × (−13.8378) + (208722_s_at) × (−11.2409) + (218593_at) × (−15.2664) + (221494_x_at) × 25.3464 + (222011_s_at) × (22.8465)

Equation for calculation of probability of low risk for distant metastasis:

$$\eta = \log it(\pi) \equiv \log\left(\frac{\pi}{1-\pi}\right) = \alpha + \beta' X$$

is estimated by $\hat{\eta} = \hat{\alpha} + \hat{\beta}' X \Rightarrow \hat{\pi} = \dfrac{1}{1 + e^{-\hat{\eta}}}$ η: logit score; π: probability for low risk of distant metastasis
α: constant; β': coefficient; X: normalized intensity of each probe set.
Affymetrix probe set identification numbers in parentheses represent the normalized expression intensity of the mRNA transcript for the indicated probe sets. Logit score calculated from the listed equation was used to estimate the probability of low risk for distant metastasis. A probability of >0.5 was regarded as low risk for distant metastasis. A probability of <0.5 was regarded as high risk.

TABLE 3

Clinical Characteristics of 138 Patients

| | Training Set | | Test Set | |
|---|---|---|---|---|
| | Low risk* | High risk** | Low risk* | High risk** |
| Number of cases | 62 | 34 | 29 | 13 |
| Sex | | | | |
| male | 40 (64.52%) | 28 (82.35%) | 19 (65.52%) | 11 (84.62%) |
| female | 22 (35.48%) | 6 (17.65%) | 10 (34.48%) | 2 (15.38%) |
| Age | | | | |
| <=45 y | 34 (54.84%) | 21 (61.76%) | 13 (44.83%) | 8 (61.54%) |
| >45 y | 28 (45.16%) | 13 (38.24%) | 16 (55.17%) | 5 (38.46%) |
| Overall TNM Stage | | | | |
| I + II | 18 (29.03%) | 1 (3.03%) | 8 (27.59%) | 1 (7.69%) |
| III + IV | 44 (70.97%) | 32 (96.97%) | 21 (72.41%) | 12 (92.31%) |
| Follow-up Duration* | | | | |
| >4.5 y | 18 (29.03%) | 2 (5.88%) | 7 (24.14%) | 0 (0.00%) |
| 4.5-3 y | 44 (70.97%) | 1 (2.94%) | 22 (75.86%) | 2 (15.38%) |
| <=3 y | | 31 (91.18%) | | 11 (84.62%) |
| Time to metastasis | | | | |
| <=1.5 y | | 28 (82.35%) | | 11 (84.62%) |
| >1.5 y | | 6 (17.65%) | | 2 (15.38%) |
| Year of biopsy | | | | |
| 1992-1997 | 3 (5%) | 1 (3%) | 1 (3%) | 1 (8%) |
| 1998-1999 | 24 (39%) | 6 (18%) | 11 (38%) | 0 (0%) |
| 2000-2001 | 35 (56%) | 14 (41%) | 17 (59%) | 7 (54%) |
| 2002-2004 | 0 (0.00%) | 13 (38%) | 0 (0.00%) | 5 (38%) |

*All clinically low risk cases had been followed up for more than 3 years and did not develop distant metastasis.
**All clinically high risk cases had developed distant metastasis within three years after initial therapy.
There were no statistical significant differences in patient distribution between training and test sets for the listed parameters.

TABLE 4

Nine clusters of genes selected for prediction of distant metastasis

| Probe Set ID | Cluster | Gene Symbol | Gene Title | Function |
| --- | --- | --- | --- | --- |
| 200640_at | 1a | YWHAZ | tyrosine 3-monooxygenase/tryptophan 5-monooxygenase activation protein, zeta polypeptide | Lipid metabolism/signal transduction |
| 213175_s_at | 1a | SNRPB | small nuclear ribonucleoprotein polypeptides B and B1 | mRNA Processing |
| 202397_at | 1a | NUTF2 | nuclear transport factor 2 | Nuclear transport |
| 212247_at | 1a | NUP205 | nucleoporin 205 kDa | Nuclear transport |
| 208699_x_at | 1a | TKT | transketolase (Wernicke-Korsakoff syndrome) | Nucleotide meabolism, pentose phosphate pathway |
| 214431_at | 1a | GMPS | guanine monphosphate synthetase | Nucleotide metabolism |
| 200910_at | 1a | CCT3 | chaperonin containing TCP1, subunit 3 (gamma) | Protein Folding |
| 222011_s_at | 1a | TCP1 | t-complex 1 | Protein Folding |
| 208114_s_at | 1a | FLJ12671 | hypothetical protein FLJ12671 | Unknown |
| 215157_x_at | 1b | PABPC1 | poly(A) binding protein, cytoplasmic 1 | mRNA Processing |
| 201892_s_at | 1b | IMPDH2 | IMP (inosine monophosphate) dehydrogenase 2 | Nucleotide metabolism |
| 217870_s_at | 1b | UMP-CMPK | UMP-CMP kinase | Nucleotide metabolism |
| 218973_at | 1b | EFTUD1 | elongation factor Tu GTP binding domain containing 1 | Protein synthesis |
| 221494_x_at | 1b | EIF3S12 | eukaryotic translation initiation factor 3, subunit 12 | Protein synthesis |
| 200976_s_at | 2 | TAX1BP1 | Tax1 (human T-cell leukemia virus type I) binding protein 1 | Anti-apoptosis |
| 217917_s_at | 2 | DNCL2A | dynein, cytoplasmic, light polypeptide 2A | Cytokinesis |
| 205434_s_at | 2 | AAK1 | AP2 associated kinase 1 | Signal Transduction |
| 213408_s_at | 2 | PIK4CA | phosphatidylinositol 4-kinase, catalytic, alpha polypeptide | Signal Transduction |
| 221971_x_at | 2 | FLJ00312 | similar to ARF GTPase-activating protein | Signal Transduction |
| 211974_x_at | 2 | RBPSUH | recombining binding protein suppressor of hairless (*Drosophila*) | Transcription regulation |
| 201642_at | 3a | IFNGR2 | interferon gamma receptor 2 (interferon gamma transducer 1) | Signal Transduction-Immune response |
| 202301_s_at | 3a | FLJ11021 | similar to splicing factor, arginine/serine-rich 4 | mRNA Processing |
| 208698_s_at | 3a | NONO | non-POU domain containing, octamer-binding | mRNA Processing |
| 211115_x_at | 3a | SIP1 | survival of motor neuron protein interacting protein 1 | mRNA Processing |
| 211575_s_at | 3a | UBE3A | ubiquitin protein ligase E3A (human papilloma virus E6-associated protein, Angelman syndrome) | Protein catabolism |
| 201123_s_at | 3a | EIF5A | eukaryotic translation initiation factor 5A | Protein synthesis |
| 211913_s_at | 3a | MERTK | c-mer proto-oncogene tyrosine kinase | Signal Transduction |
| 206544_x_at | 3a | SMARCA2 | SWI/SNF related, matrix associated, actin dependent regulator of chromatin, subfamily a, member 2 | Transcription regulation |
| 212398_at | 3b | RDX | radixin | Cytokinesis |
| 208765_s_at | 3b | HNRPR | heterogeneous nuclear ribonucleoprotein R | mRNA Processing |
| 209157_at | 3b | DNAJA2 | DnaJ (Hsp40) homolog, subfamily A, member 2 | Protein Folding |
| 200880_at | 3b | DNAJA1 | DnaJ (Hsp40) homolog, subfamily A, member 1 | Unknown (HSP40 homolog) |
| 64418_at | 4a | AP!GBP1 | CDNA FLJ34482 fis, clone HLUNG2004067 | Endocyosis, intracellular protein traansport |
| 201178_at | 4a | FBXO7 | F-box protein 7 | Protein catabolism |
| 212911_at | 4a | KIAA0962 | KIAA0962 protein | Unknown (HSP40 homolog) |
| 213254_at | 4a | TNRC6B | trinucleotide repeat containing 6B | Unknown (HSP40 homolog) |
| 217969_at | 4a | C11orf2 | chromosome 11 open reading frame2 | Unknown (membrane protein) |
| 218659_at | 4a | ASXL2 | additional sex combs like 2 (*Drosophila*) | Unknown (polycomb) |
| 212884_x_at | 4b | APOE | apolipoprotein E | Lipid metabolsm (ApoE) |
| 202211_at | 4b | ARFGAP3 | ADP-ribosylation factor GTPase activating protein 3 | Signal Transduction |
| 221269_s_at | 4b | SH3BGRL3 | SH3 domain binding glutamic acid-rich protein like 3 | Signal transduction, Thioredoxin superfamily, TNFalpha-inhibitory protein |
| 207335_x_at | 5 | ATP5I | ATP synthase, H+ transporting, mitochondrial F0 complex, subunit e | ATP synthesis |
| 211733_x_at | 5 | SCP2 | sterol carrier protein 2 | Lipid metabolism/signal transduction |
| 209584_x_at | 5 | APOBEC3C | apolipoprotein B mRNA editing enzyme, catalytic polypeptide-like 3C | mRNA processing |
| 200921_s_at | 5 | BTG1 | B-cell translocation gene 1, anti-proliferative | Signal transduction, anti-proliferation |
| 201057_s_at | 5 | GOLGB1 | golgi autoantigen, golgin subfamily b, macrogolgin (with transmembrane signal), 1 | Transcription regulation |
| 217118_s_at | 5 | C22orf9 | chromosome 22 open reading frame 9 | Unknown |
| 202905_x_at | 6 | NBS1 | Nijmegen breakage syndrome 1 (nibrin) | Cell cycle |
| 206559_x_at | 6 | EEF1A1 | eukaryotic translation elongation factor 1 alpha 1 | Protein synthesis |
| 201266_at | 6 | TXNRD1 | thioredoxin reductase 1 | Signal Transduction |
| 203006_at | 6 | INPP5A | inositol polyphosphate-5-phosphatase, 40 kDa | Signal Transduction |
| 212295_s_at | 6 | SLC7A1 | solute carrier family 7 (cationic amino acid transporter, y+ system), member 1 | Transport-aminoacid |

TABLE 5

Twelve genes for prediction of distant metastasis by logistic regression

| Probe Set ID | Gene Symbol | Gene Title | Function |
| --- | --- | --- | --- |
| 200057_s_at | NONO | non-POU domain containing, octamer-binding | mRNA processing |
| 208699_x_at | TKT | transketolase (Wernicke-Korsakoff syndrome) | nucleotide metabolism, pentose phosphate pathway |
| 201892_s_at | IMPDH2 | IMP (inosine monophosphate) dehydrogenase 2 | nucleotide biosynthesis |
| 200842_s_at | EPRS | glutamyl-prolyl-tRNA synthetase | protein biosynthesis |
| 221494_x_at | EIF3S12 | eukaryotic translation initiation factor 3, subunit12 | protein biosynthesis |
| 201947_s_at | CCT2 | chaperonin containing TCP1, subunit 2 (beta) | protein folding |
| 200910_at | CCT3 | chaperonin containing TCP1, subunit 3 (gamma) | protein folding |
| 222011_s_at | TCP1 | chaperonin containing TCP1, subunit 1 (alpha) | protein folding |
| 208722_s_at | ANAPC5 | anaphase promoting complex subunit 5 | ubiquitin-dependent protein catabolism/cell cycle |
| 201948_at | GNL2 | guanine nucleotide binding protein-like 2 nucleolar | ribosome biogenesis |
| 218593_at | RBM28 | RNA binding motif protein 28 | ribosome biogenesis |
| 208114_s_at | FLJ12671 | hypothetical protein FLJ12671 | unknown |

Highlighted genes are not present in the list of Table 4.

TABLE 6

Concordance of predicted results based on 52 and 12 genes.

| Case Number | Clinical Risk Group | 52-genes Prediction | 12-genes Prediction | Combined Results |
| --- | --- | --- | --- | --- |
| 1 | 0* | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 0 | 0 | 0 | 0 |
| 8 | 0 | 0 | 0 | 0 |
| 9 | 0 | 0 | 0 | 0 |
| 10 | 0 | 0 | 0 | 0 |
| 11 | 0 | 0 | 0 | 0 |
| 12 | 0 | 0 | 0 | 0 |
| 13 | 0 | 0 | 0 | 0 |
| 14 | 0 | 0 | 0 | 0 |
| 15 | 0 | 0 | 0 | 0 |
| 16 | 0 | 0 | 0 | 0 |
| 17 | 0 | 0 | 0 | 0 |
| 18 | 0 | 0 | 0 | 0 |
| 19 | 0 | 0 | 0 | 0 |
| 20 | 0 | 0 | 0 | 0 |
| 21 | 0 | 1 | 0 | 9*** |
| 22 | 0 | 0 | 1 | 9 |
| 23 | 0 | 0 | 1 | 9 |
| 24 | 0 | 0 | 1 | 9 |
| 25 | 0 | 0 | 1 | 9 |
| 26 | 0 | 0 | 1 | 9 |
| 27 | 0 | 1 | 1 | 1 |
| 28 | 0 | 1 | 1 | 1 |
| 29 | 0 | 1 | 1 | 1 |
| 30 | 1** | 1 | 1 | 1 |
| 31 | 1 | 0 | 0 | 0 |
| 32 | 1 | 0 | 1 | 9 |
| 33 | 1 | 0 | 1 | 9 |
| 34 | 1 | 1 | 1 | 1 |
| 35 | 1 | 1 | 1 | 1 |
| 36 | 1 | 1 | 1 | 1 |
| 37 | 1 | 1 | 1 | 1 |
| 38 | 1 | 1 | 1 | 1 |
| 39 | 1 | 1 | 1 | 1 |
| 40 | 1 | 1 | 1 | 1 |
| 41 | 1 | 1 | 1 | 1 |
| 42 | 1 | 0 | 0 | 0 |

*"0" means low risk for distant metastasis;
**"1" means high risk for distant metastasis;
***"9" means discordance between two predictive methods.

The entire disclosures of all applications, patents and publications, cited herein are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of assessing the risk of distant metastasis in a patient having nasopharyngeal carcinoma comprising evaluating, in a sample from said patient, the expression profile of a combination of genes comprising
   (i) tyrosine 3-monooxygenase/tryptophan 5-monooxygenase activation protein, zeta polypeptide (YWHAZ);
   (ii) small nuclear ribonucleoprotein polypeptides B and B1 (SNRPB);
   (iii) nuclear transport factor 2 (NUTF2);
   (iv) nucleoporin 205kDa (NUP205);
   (v) transketolase (TKT);
   (vi) guanine monphosphate synthetase (GMPS);
   (vii) chaperonin containing TCP1, subunit 3 γ (CCT3);
   (viii) t-complex 1 (TCP1);
   (ix) hypothetical protein FLJ12671 (FLJ12671);
   (x) poly(A) binding protein, cytoplasmic 1 (PABPC1);
   (xi) IMP (inosine monophosphate) dehydrogenase 2 (IMPDH2);
   (xii) UMP-CMP kinase (UMP-CMPK);
   (xiii) elongation factor Tu GTP binding domain containing 1 (EFTUD1);
   (xiv) eukaryotic translation initiation factor 3, subunit 12 (EIF3S12);
   (xv) Tax1 (human T-cell leukemia virus type I) binding protein 1 (TAX1BP1);
   (xvi) dynein, cytoplasmic, light polypeptide 2A (DNCL2A);
   (xvii) AP2 associated kinase 1 (AAK1);
   (xviii) phosphatidylinositol 4-kinase, catalytic, alpha polypeptide (PIK4CA);
   (xix) ARF GTPase-activating protein (FLJ00312);
   (xx) recombining binding protein suppressor of hairless (RBPSUH);

(xxi) interferon gamma receptor 2 (IFNGR2);
(xxii) splicing factor, arginine/serine-rich 4 (FLJ11021);
(xxiii) non-POU domain containing, octamer-binding (NONO);
(xxiv) survival of motor neuron protein interacting protein 1(SIP1);
(xxv) ubiquitin protein ligase E3A (UBE3A);
(xxvi) eukaryotic translation initiation factor 5A (EIF5A);
(xxvii) c-mer proto-oncogene tyrosine kinase (MERTK);
(xxviii) SWI/SNF related, matrix associated, actin dependent regulator of chromatin, subfamily a, member 2 (SMARCA2);
(xxix) Radixin (RDX);
(xxx) heterogeneous nuclear ribonucleoprotein R (HNRPR);
(xxxi) DnaJ (Hsp40) homolog, subfamily A, member 2 (DNAJA2);
(xxxii) DnaJ (Hsp40) homolog, subfamily A, member 1(DNAJA1);
(xxxiii) CDNA FLJ34482 fis, clone HLUNG2004067 (AP!GBP1);
(xxxiv) F-box protein 7 (FBXO7);
(xxxv) KIAA0962 protein (KIAA0962);
(xxxvi) trinucleotide repeat containing 6B (TNRC6B);
(xxxvii) chromosome 11 open reading frame2 (C11orf2);
(xxxviii) additional sex combs like 2 (ASXL2);
(xxxix) apolipoprotein E (APOE);
(xl) ADP-ribosylation factor GTPase activating protein 3 (ARFGAP3);
(xli) SH3 domain binding glutamic acid-rich protein like 3 (SH3BGRL3);
(xlii) ATP synthase, H+transporting, mitochondrial F0 complex, subunit e (ATP5I);
(xliii) sterol carrier protein 2 (SCP2);
(xliv) apolipoprotein B mRNA editing enzyme, catalytic polypeptide-like 3C (APOBEC3C);
(xlv) B-cell translocation gene 1, anti-proliferative (BTG1);
(xlvi) golgi autoantigen, golgin subfamily b, macrogolgin (with transmembrane signal), 1 (GOLGB1);
(xlvii) chromosome 22 open reading frame 9 (C22orf9);
(xlviii) Nijmegen breakage syndrome 1 (NBS1);
(xlix) eukaryotic translation elongation factor 1 alpha 1 (EEF1A1);
(l) thioredoxin reductase 1 (TXNRD1 );
(li) inositol polyphosphate-5 -phosphatase, 40 kDa (INPP5A);
(lii) solute carrier family 7 (cationic amino acid transporter, y+ system), member 1 (SLC7A1);
(liii) IMP (inosine monophosphate) dehydrogenase 2 (IMPDH2);
(liv) glutamyl-prolyl-tRNA synthetase (EPRS);
(lv) chaperonin containing TCP1, subunit 2 β (CCT2);
(lvi) chaperonin containing TCP1, subunit 1 α (TCP1);
(lvii) anaphase promoting complex subunit 5 (ANAPC5);
(lviii) nucleolar guanine nucleotide binding protein-like 2 (GNL2); and
(lix) RNA binding motif protein 28 (RBM28).

2. A method according to claim 1 wherein said expression profile is evaluated in an NPC tumor specimen.

3. A method according to claim 1 wherein said expression profile is generated from mRNA transcripts.

4. A method of assessing the risk of distant metastasis in a patient having nasopharyngeal carcinoma comprising evaluating the expression profiles of a combination of genes in a sample from said patient comprising
(i) tyrosine 3-monooxygenase/tryptophan 5-monooxygenase activation protein, zeta polypeptide (YWHAZ);
(ii) small nuclear ribonucleoprotein polypeptides B and B1 (SNRPB);
(iii) nuclear transport factor 2 (NUTF2);
(iv) nucleoporin 205kDa (NUP205);
(v) transketolase (TKT);
(vi) guanine monphosphate synthetase (GMPS);
(vii) chaperonin containing TCP1, subunit 3 γ (CCT3);
t-complex 1 (TCP1);
(ix) hypothetical protein FLJ12671 (FLJ12671);
(x) poly(A) binding protein, cytoplasmic 1 (PABPC1);
(xi) IMP (inosine monophosphate) dehydrogenase 2 (IMPDH2);
(xii) UMP-CMP kinase (UMP-CMPK);
(xiii) elongation factor Tu GTP binding domain containing 1 (EFTUD1);
(xiv) eukaryotic translation initiation factor 3, subunit 12 (EIF3S12);
(xv) Tax1 (human T-cell leukemia virus type I) binding protein 1 (TAX1BP1);
(xvi) dynein, cytoplasmic, light polypeptide 2A (DNCL2A);
(xvii) AP2 associated kinase 1 (AAK1);
phosphatidylinositol 4-kinase, catalytic, alpha polypeptide (PIK4CA);
(xix) ARF GTPase-activating protein (FLJ00312);
(xx) recombining binding protein suppressor of hairless (RBPSUH);
(xxi) interferon gamma receptor 2 (IFNGR2);
(xxii) splicing factor, arginine/serine-rich 4 (FLJ11021);
non-POU domain containing, octamer-binding (NONO);
(xxiv) survival of motor neuron protein interacting protein 1(SIP1);
(xxv) ubiquitin protein ligase E3A (UBE3A);
(xxvi) eukaryotic translation initiation factor 5A (EIF5A);
(xxvii) c-mer proto-oncogene tyrosine kinase (MERTK);
(xxviii) SWI/SNF related, matrix associated, actin dependent regulator of chromatin, subfamily a, member 2 (SMARCA2);
(xxix) Radixin (RDX);
(xxx) heterogeneous nuclear ribonucleoprotein R (HNRPR);
(xxxi) DnaJ (Hsp40) homolog, subfamily A, member 2 (DNAJA2);
(xxxii) DnaJ (Hsp40) homolog, subfamily A, member 1(DNAJA1);
(xxxiii) CDNA FLJ34482 fis, clone HLUNG2004067 (AP!GBP1);
(xxxiv) F-box protein 7 (FBXO7);
(xxxv) KIAA0962 protein (KIAA0962);
(xxxvi) trinucleotide repeat containing 6B (TNRC6B);
(xxxvii) chromosome 11 open reading frame2 (C11orf2);
(xxxviii) additional sex combs like 2 (ASXL2);
(xxxix) apolipoprotein E (APOE);
(xl) ADP-ribosylation factor GTPase activating protein 3 (ARFGAP3);
(xli) SH3 domain binding glutamic acid-rich protein like 3 (SH3BGRL3);
(xlii) ATP synthase, H+ transporting, mitochondrial F0 complex, subunit e (ATP5I);
(xliii) sterol carrier protein 2 (SCP2);
(xliv) apolipoprotein B mRNA editing enzyme, catalytic polypeptide-like 3C (APOBEC3C);
(xlv) B-cell translocation gene 1, anti-proliferative (BTG1);
(xlvi) golgi autoantigen, golgin subfamily b, macrogolgin (with transmembrane signal), 1 (GOLGB1);
(xlvii) chromosome 22 open reading frame 9 (C22orf9);
(xlviii) Nijmegen breakage syndrome 1 (NBS1);

(xlix) eukaryotic translation elongation factor 1 alpha 1 (EEF1A1);
(l) thioredoxin reductase 1 (TXNRD1);
(li) inositol polyphosphate-5-phosphatase, 40kDa (INPP5A); and
(lii) solute carrier family 7 (cationic amino acid transporter, y+ system), member 1 (SLC7A1).

5. A method according to claim 4 wherein the evaluation of the expression of the 52 genes is performed using a regression model for clusters of genes, wherein said clusters comprise:
(a) cluster 1a comprises genes (i)-(ix) of claim 4;
(b) cluster 1b comprises genes (x)-(xiv) of claim 4;
(c) cluster 2 comprises genes (xv)-(xx) of claim 4;
(d) cluster 3a comprises genes (xxi)-(xxviii) of claim 4;
(e) cluster 3b comprises genes (xxix)-(xxxii) of claim 4;
(f) cluster 4a comprises genes (xxxiii)-(xxxviii) of claim 4;
(g) cluster 4b comprises genes (xxxix)-(xli) of claim 4;
(h) cluster 5 comprises genes (xlii)-(xlvii) of claim 4; and
(i) cluster 6 comprises genes (xlviii)-(lii) of claim 4.

6. A method according to claim 5 comprising generating a logit score for each of the nine gene clusters using a regression model equation which is LOGIT Ia=(200640_at)×4.6445+(200910_at)×(−4.9525)+(202397_at)×3.6645+(208114_s_at)×5.4097+(208699_x_at)×2.9153+(212247_at)×2.2052+(213175_s_at)×3.4262+(214431_at)×(−3.4637)+(222011_s_at)×4.4282−183.906;

LOGIT Ib=(201892_s_at)×2.0433+(215157_x_at)×3.0064+(217870_s_at)×2.1101+(218973_at)×4.07+(221494_x_at)×(−3.6926)−79.0097;

LOGIT II=(200976_s_at)×(−3.8876)+(205434_s_at0×(−1.8483)+(211974_x_at)×(−3.3451)+(213408_s_at)×(−3.8384)+(217917_s_a)×(−5.3073)+(221971_x_at)×7.0464+126.459;

LOGIT IIIa=(201123_s_at)×0.8651+(201642_at)×3.9114+(202301_s_at)×7.9516+(206544_x_at)×(−1.8805)+(208698_s_at)×2.8301+(211115_x_at)×4.0432+(211575_s_at)×(−4.3726)+(211913_s_at)×(−2.2606)−117.98;

LOGIT IIIb=(200880_at)×2.7955+(208765_s_at)×2.1072+(209157_at)×2.2478+(212398_at)×3.4807−104.518;

LOGIT IVa=(201178_at)×(−2.6194)+(212911_at)×(−2.4526)+(213254_at)×(−1.7758)+(217969_at)×2.475+(218659_at)×3.3188+(64418_at)×(−2.4296)+22.4303;

LOGIT IVb=(202211_at)×(−2.1207)+(212884_x_at)×(−1.0461)+(221269_s_at)×(−0.9598)+40.9722;

LOGIT V=(200921_s_at)×(−2.6385)+(201057_s_at)×(−2.5845)+(207335_x_at)×(−2.7044)+(209584_x_at)×(−1.6973)+(211733_x_at)×(−4.2067)+(217118_s_at)×(−2.539)+171.7096;

LOGIT VI=(201266_at)×2.5851+(202905_x_at)×2.7306+(203006_at)×1.6767+(206559_x_at)×13.1357+(212295_s_at)×2.7269−286.114.

7. A method according to claim 6, comprising further generating a predictive rule for risk of distant metastasis by applying to said logit scores for said nine gene clusters a k-nearest neighbors classifying method.

8. A method according to claim 7 wherein the risk of distant metastasis resulting from said predictive rule is compared with the risk of distant metastasis from a second independent predictive rule which evaluates said risk using the equation $$[\text{Probability for low risk of distant metastasis}] \frac{1}{1 + e^{-(\text{logit score})}}.$$

wherein logit score is generated using a regression model equation which is $$\log it(\pi) = 459.9 + (200057\_s\_at) \times (-12.5305) + (200842\_s\_at) \times 12.3230 + (200910\_at) \times 21.4064 + (201892\_s\_at) \times (-10.5046) + (201947\_s\_at) \times 20.0446 + (201948\_at) \times (-17.7163) + (208114\_s\_at) \times (-35.1981) + (208699\_x\_at) \times (-13.8378) + (208722\_s\_at) \times (-11.2409) + (218593\_at) \times (-15.2664) + (221494\_x\_at) \times 25.3464 + (222011\_s\_at) \times (-22.8465);$$

and said logit score is correlated with risk of distant metastasis using the equation $$\eta = \log it(\pi) \equiv \log\left(\frac{\pi}{1-\pi}\right) = \alpha + \beta' X,$$

which is estimated by $$\hat{\eta} = \hat{\alpha} + \hat{\beta}' X \Rightarrow \hat{\pi} = \frac{1}{1 + e^{-\hat{\eta}}},$$

wherein,
η is logit score;
π is probability for low risk of distant metastasis;
α is a constant;
β is coefficient;
X is normalized intensity of each probe set, and the method further comprises evaluating the expression profiles of the 12 genes which are
(i) non-POU domain containing, octamer-binding (NONO);
(ii) transketolase (TKT);
(iii) IMP (inosine monophosphate) dehydrogenase 2 (IMPDH2);
(iv) glutamyl-prolyl-tRNA synthetase (EPRS);
(v) eukaryotic translation initiation factor 3, subunit12 (EIF3S12);
(vi) chaperonin containing TCP1, subunit 2 β (CCT2);
(vii) chaperonin containing TCP1, subunit 3 γ (CCT3);
(viii) chaperonin containing TCP1, subunit 1 α a (TCP1);
(ix) anaphase promoting complex subunit 5 (ANAPC5);
(x) nucleolar guanine nucleotide binding protein-like 2 (GNL2);
(xi) RNA binding motif protein 28 (RBM28); and
(xii) hypothetical protein FLJ12671 (FLJ12671).

9. A method according to claim 8 wherein when the risk of distant metastasis determined from both of said methods is low or high, then the risk is scored as low or high, respectively, and when said determined risks are discordant, then the risk is scored as indeterminate.

10. A method of assessing the risk of distant metastasis in a patient having nasopharyngeal carcinoma comprising evaluating the expression profile of a combination of genes in a sample from said patient comprising
(i) non-POU domain containing, octamer-binding (NONO);
transketolase (TKT);
(iii) IMP (inosine monophosphate) dehydrogenase 2 (IMPDH2);
(iv) glutamyl-prolyl-tRNA synthetase (EPRS);
(v) eukaryotic translation initiation factor 3, subunit12 (EIF3S12);
(vi) chaperonin containing TCP1, subunit 2 β (CCT2);

(vii) chaperonin containing TCP1, subunit 3 γ (CCT3);
(viii) chaperonin containing TCP1, subunit 1 α (TCP1);
(ix) anaphase promoting complex subunit 5 (ANAPC5);
(x) nucleolar guanine nucleotide binding protein-like 2 (GNL2);
(xi) RNA binding motif protein 28 (RBM28); and
(xii) hypothetical protein FLJ12671 (FLJ12671).

11. A method according to claim 10, further comprising evaluating the expression of the 12 genes using a logistic regression model.

12. A method according to claim 11, comprising generating a logit score based on the expression profiles of said 12 genes using a regression model equation which is $$\log it(\pi) = 459.9 + (200057\_s\_at) \times (-12.5305) + (200842\_s\_at) \times 12.3230 + (200910\_at) \times 21.4064 + (201892\_s\_at) \times (-10.5046) + (201947\_s\_at) \times 20.0446 + (201948\_at) \times (-17.7163) + (208114\_s\_at) \times (-35.1981) + (208699\_x\_at) \times (-13.8378) + (208722\_s\_at) \times (-11.2409) + (218593\_at) \times (-15.2664) + (221494\_x\_at) \times 25.3464 + (222011\_s\_at) \times (-22.8465)$$

and said logit score is correlated with risk of distant metastasis using the equation $$\eta = \log it(\pi) \equiv \log\left(\frac{\pi}{1-\pi}\right) = \alpha + \beta' X,$$

which is estimated by $$\hat{\eta} = \hat{\alpha} + \hat{\beta}' X \Rightarrow \hat{\pi} = \frac{1}{1+e^{-\hat{\eta}}},$$

wherein
η is logit score;
π is probability for low risk of distant metastasis;
α is a constant;
β is coefficient;
X is normalized intensity of each probe set.

13. A method according to claim 12 wherein predictive rule for low risk of distant metastasis is $$[\text{Probability for low risk of distant metastasis}] = \frac{1}{1+e^{-(logit\ score)}}.$$

14. A nucleic acid microarray useful for determining the risk of distant metastasis in a patient having nasopharyngeal carcinoma consisting essentially of probes for determining the expression profiles of
(I) Set A comprising 52 genes which are
  (i) tyrosine 3-monooxygenase/tryptophan 5-monooxygenase activation protein, zeta polypeptide (YWHAZ);
  (ii) small nuclear ribonucleoprotein polypeptides B and B1 (SNRPB);
  (iii) nuclear transport factor 2 (NUTF2);
  (iv) nucleoporin 205kDa (NUP205);
  (v) transketolase (TKT);
  (vi) guanine monphosphate synthetase (GMPS);
  (vii) chaperonin containing TCP1, subunit 3 γ (CCT3);
  (viii) t-complex 1 (TCP1);
  (ix) hypothetical protein FLJ12671 (FLJ12671);
  (x) poly(A) binding protein, cytoplasmic 1 (PABPC1);
  (xi) IMP (inosine monophosphate) dehydrogenase 2 (IMPDH2);
  (xii) UMP-CMP kinase (UMP-CMPK);
  (xiii) elongation factor Tu GTP binding domain containing 1 (EFTUD1);
  (xiv) eukaryotic translation initiation factor 3, subunit 12 (EIF3S12);
  (xv) Tax1 (human T-cell leukemia virus type I) binding protein 1 (TAX1BP1);
  (xvi) dynein, cytoplasmic, light polypeptide 2A (DNCL2A);
  (xvii) AP2 associated kinase 1 (AAK1);
  (xviii) phosphatidylinositol 4-kinase, catalytic, alpha polypeptide (PIK4CA);
  (xix) ARF GTPase-activating protein (FLJ00312);
  (xx) recombining binding protein suppressor of hairless (RBPSUH);
  (xxi) interferon gamma receptor 2 (IFNGR2);
  (xxii) splicing factor, arginine/serine-rich 4 (FLJ11021);
  (xxiii) non-POU domain containing, octamer-binding (NONO);
  (xxiv) survival of motor neuron protein interacting protein 1(SIP1);
  (xxv) ubiquitin protein ligase E3A (UBE3A);
  (xxvi) eukaryotic translation initiation factor 5A (EIF5A);
  (xxvii) c-mer proto-oncogene tyrosine kinase (MERTK);
  (xxviii) SWI/SNF related, matrix associated, actin dependent regulator of chromatin, subfamily a, member 2 (SMARCA2);
  (xxix) Radixin (RDX);
  (xxx) heterogeneous nuclear ribonucleoprotein R (HNRPR);
  (xxxi) DnaJ (Hsp40) homolog, subfamily A, member 2 (DNAJA2);
  (xxxii) DnaJ (Hsp40) homolog, subfamily A, member 1(DNAJA1);
  (xxxiii) CDNA FLJ34482 fis, clone HLUNG2004067 (AP!GBP1);
  (xxxiv) F-box protein 7 (FBXO7);
  (xxxv) KIAA0962 protein (KIAA0962);
  (xxxvi) trinucleotide repeat containing 6B (TNRC6B);
  (xxxvii) chromosome 11 open reading frame2 (C11orf2);
  (xxxviii) additional sex combs like 2 (ASXL2);
  (xxxix) apolipoprotein E (APOE);
  (xl) ADP-ribosylation factor GTPase activating protein 3 (ARFGAP3);
  (xli) SH3 domain binding glutamic acid-rich protein like 3 (SH3BGRL3);
  (xlii) ATP synthase, H+transporting, mitochondrial F0 complex, subunit e (ATP5I);
  (xliii) sterol carrier protein 2 (SCP2);
  (xliv) apolipoprotein B mRNA editing enzyme, catalytic polypeptide-like 3C (APOBEC3C);
  (xlv) B-cell translocation gene 1, anti-proliferative (BTG1);
  (xlvi) golgi autoantigen, golgin subfamily b, macrogolgin (with transmembrane signal), 1 (GOLGB1);
  (xlvii) chromosome 22 open reading frame 9 (C22orf9);
  (xlviii) Nijmegen breakage syndrome 1 (NBS1);
  (xlix) eukaryotic translation elongation factor 1 alpha 1 (EEF1A1);
  (l) thioredoxin reductase 1 (TXNRD1);
  (li) inositol polyphosphate-5-phosphatase, 40kDa (INPP5A); and (lii) solute carrier family 7 (cationic amino acid transporter, γ+ system), member 1 (SLC7A1);
or
(II) Set B comprising 12 genes which are
(i) non-POU domain containing, octamer-binding (NONO);
transketolase (TKT);
(iii) IMP (inosine monophosphate) dehydrogenase 2 (IMPDH2);
(iv) glutamyl-prolyl-tRNA synthetase (EPRS);
(v) eukaryotic translation initiation factor 3, subunit12 (EIF3S12);
(vi) chaperonin containing TCP1, subunit 2 β (CCT2);
(vii) chaperonin containing TCP1, subunit 3 γ (CCT3);
(viii) chaperonin containing TCP1, subunit 1 α (TCP1);
(ix) anaphase promoting complex subunit 5 (ANAPC5);
(x) nucleolar guanine nucleotide binding protein-like 2 (GNL2);
(xi) RNA binding motif protein 28 (RBM28); and
(xii) hypothetical protein FLJ12671 (FLJ12671);
or
(III) both said sets A and B.

15. A kit comprising an array of probes for detecting nucleic acids from at least one set which is Set (A), Set (B) or Set (C) optionally together with regents and instructions for detection, wherein
Set (A) comprises all 52 genes which are
(i) tyrosine 3-monooxygenase/tryptophan 5-monooxygenase activation protein, zeta polypeptide (YWHAZ);
(ii) small nuclear ribonucleoprotein polypeptides B and B1 (SNRPB);
(iii) nuclear transport factor 2 (NUTF2);
(iv) nucleoporin 205kDa (NUP205);
(v) transketolase (TKT);
(vi) guanine monphosphate synthetase (GMPS);
(vii) chaperonin containing TCP1, subunit 3 γ (CCT3);
(viii) t-complex 1 (TCP1);
(ix) hypothetical protein FLJ12671 (FLJ12671);
(x) poly(A) binding protein, cytoplasmic 1 (PABPC1);
(xi) IMP (inosine monophosphate) dehydrogenase 2 (IMPDH2);
(xii) UMP-CMP kinase (UMP-CMPK);
(xiii) elongation factor Tu GTP binding domain containing 1 (EFTUD1);
(xiv) eukaryotic translation initiation factor 3, subunit 12 (EIF3S12);
(xv) Tax1 (human T-cell leukemia virus type I) binding protein 1 (TAX1BP1);
(xvi) dynein, cytoplasmic, light polypeptide 2A (DNCL2A);
(xvii) AP2 associated kinase 1 (AAK1);
(xviii) phosphatidylinositol 4-kinase, catalytic, alpha polypeptide (PIK4CA);
(xix) ARF GTPase-activating protein (FLJ00312);
(xx) recombining binding protein suppressor of hairless (RBPSUH);
(xxi) interferon gamma receptor 2 (IFNGR2);
(xxii) splicing factor, arginine/serine-rich 4 (FLJ11021);
(xxiii) non-POU domain containing, octamer-binding (NONO);
(xxiv) survival of motor neuron protein interacting protein 1 (SIP1);
(xxv) ubiquitin protein ligase E3A (UBE3A);
(xxvi) eukaryotic translation initiation factor 5A (EIF5A);
(xxvii) c-mer proto-oncogene tyrosine kinase (MERTK);
(xxviii) SWI/SNF related, matrix associated, actin dependent regulator of chromatin, subfamily a, member 2 (SMARCA2);
(xxix) Radixin (RDX);
(xxx) heterogeneous nuclear ribonucleoprotein R (HNRPR);
(xxxi) DnaJ (Hsp40) homolog, subfamily A, member 2 (DNAJA2);
(xxxii) DnaJ (Hsp40) homolog, subfamily A, member 1 (DNAJA1);
(xxxiii) CDNA FLJ34482 fis, clone HLUNG2004067 (AP!GBP1);
(xxxiv) F-box protein 7 (FBXO7);
(xxxv) KIAA0962 protein (KIAA0962);
(xxxvi) trinucleotide repeat containing 6B (TNRC6B);
(xxxvii) chromosome 11 open reading frame2 (C11orf2);
(xxxviii) additional sex combs like 2 (ASXL2);
(xxxix) apolipoprotein E (APOE);
(xl) ADP-ribosylation factor GTPase activating protein 3 (ARFGAP3);
(xli) SH3 domain binding glutamic acid-rich protein like 3 (SH3BGRL3);
(xlii) ATP synthase, H+transporting, mitochondrial F0 complex, subunit e (ATP5I);
(xliii) sterol carrier protein 2 (SCP2);
(xliv) apolipoprotein B mRNA editing enzyme, catalytic polypeptide-like 3C (APOBEC3C);
(xlv) B-cell translocation gene 1, anti-proliferative (BTG1);
(xlvi) golgi autoantigen, golgin subfamily b, macrogolgin (with transmembrane signal), 1 (GOLGB1);
(xlvii) chromosome 22 open reading frame 9 (C22orf9);
(xlviii) Nijmegen breakage syndrome 1 (NBS1);
(xlix) eukaryotic translation elongation factor 1 alpha 1 (EEF1A1);
(l) thioredoxin reductase 1 (TXNRD1);
(li) inositol polyphosphate-5-phosphatase, 40kDa (INPP5A); and
(lii) solute carrier family 7 (cationic amino acid transporter, γ+ system), member 1 (SLC7A1);
Set (B) comprises all 12 genes which are
(i) non-POU domain containing, octamer-binding (NONO);
transketolase (TKT);
(iii) IMP (inosine monophosphate) dehydrogenase 2 (IMPDH2);
(iv) glutamyl-prolyl-tRNA synthetase (EPRS);
(v) eukaryotic translation initiation factor 3, subunit12 (EIF3S12);
(vi) chaperonin containing TCP1, subunit 2 β (CCT2);
(vii) chaperonin containing TCP1, subunit 3 γ (CCT3);
(viii) chaperonin containing TCP1, subunit 1 α (TCP1);
(ix) anaphase promoting complex subunit 5 (ANAPC5);
(x) nucleolar guanine nucleotide binding protein-like 2 (GNL2);
(xi) RNA binding motif protein 28 (RBM28); and
(xii) hypothetical protein FLJ12671 (FLJ12671); and
Set (C) comprises all the 52 genes from Set (A) and all the 12 genes from Set (B).

16. A method of assessing the risk of distant metastasis in a patient having nasopharyngeal carcinoma comprising
(A) evaluating, in a sample from said patient, the expression profile of the 52 genes which are (i) tyrosine 3-monooxygenase/tryptophan 5-monooxygenase activation protein, zeta polypeptide (YWHAZ);
(ii) small nuclear ribonucleoprotein polypeptides B and B1 (SNRPB);
(iii) nuclear transport factor 2 (NUTF2);
(iv) nucleoporin 205kDa (NUP205);
(v) transketolase (TKT);
(vi) guanine monphosphate synthetase (GMPS);
(vii) chaperonin containing TCP1, subunit 3 γ (CCT3);
(viii) t-complex 1 (TCP1);
(ix) hypothetical protein FLJ12671 (FLJ12671);
(x) poly(A) binding protein, cytoplasmic 1 (PABPC1);
(xi) IMP (inosine monophosphate) dehydrogenase 2 (IMPDH2);
(xii) UMP-CMP kinase (UMP-CMPK);
(xiii) elongation factor Tu GTP binding domain containing 1 (EFTUD1);
(xiv) eukaryotic translation initiation factor 3, subunit 12 (EIF3S12);
(xv) Tax1 (human T-cell leukemia virus type I) binding protein 1 (TAX1BP1);
(xvi) dynein, cytoplasmic, light polypeptide 2A (DNCL2A);
(xvii) AP2 associated kinase 1 (AAK1);
(xviii) phosphatidylinositol 4-kinase, catalytic, alpha polypeptide (PIK4CA);
(xix) ARF GTPase-activating protein (FLJ00312);
(xx) recombining binding protein suppressor of hairless (RBPSUH);
(xxi) interferon gamma receptor 2 (IFNGR2);
(xxii) splicing factor, arginine/serine-rich 4 (FLJ11021);
(xxiii) non-POU domain containing, octamer-binding (NONO);
(xxiv) survival of motor neuron protein interacting protein 1(SIP1);
(xxv) ubiquitin protein ligase E3A (UBE3A);
(xxvi) eukaryotic translation initiation factor 5A (EIF5A);
(xxvii) c-mer proto-oncogene tyrosine kinase (MERTK);
(xxviii) SWI/SNF related, matrix associated, actin dependent regulator of chromatin, subfamily a, member 2 (SMARCA2);
(xxix) Radixin (RDX);
(xxx) heterogeneous nuclear ribonucleoprotein R (HNRPR);
(xxxi) DnaJ (Hsp40) homolog, subfamily A, member 2 (DNAJA2);
(xxxii) DnaJ (Hsp40) homolog, subfamily A, member 1(DNAJA1);
(xxxiii) CDNA FLJ34482 fis, clone HLUNG2004067 (AP!GBP1);
(xxxiv) F-box protein 7 (FBXO7);
(xxxv) KIAA0962 protein (KIAA0962);
(xxxvi) trinucleotide repeat containing 6B (TNRC6B);
(xxxvii) chromosome 11 open reading frame2 (C11orf2);
(xxxviii) additional sex combs like 2 (ASXL2);
(xxxix) apolipoprotein E (APOE);
(xl) ADP-ribosylation factor GTPase activating protein 3 (ARFGAP3);
(xli) SH3 domain binding glutamic acid-rich protein like 3 (SH3BGRL3);
(xlii) ATP synthase, H+transporting, mitochondrial F0 complex, subunit e (ATP5I);
(xliii) sterol carrier protein 2 (SCP2);
(xliv) apolipoprotein B mRNA editing enzyme, catalytic polypeptide-like 3C (APOBEC3C);
(xlv) B-cell translocation gene 1, anti-proliferative (BTG1);
(xlvi) golgi autoantigen, golgin subfamily b, macrogolgin (with transmembrane signal), 1 (GOLGB1);
(xlvii) chromosome 22 open reading frame 9 (C22orf9);
(xlviii) Nijmegen breakage syndrome1 (NBS1);
(xlix) eukaryotic translation elongation factor 1 alpha 1 (EEF1A1);
(l) thioredoxin reductase 1 (TXNRD1);
(li) inositol polyphosphate-5-phosphatase, 40kDa (INPP5A); and
(lii) solute carrier family 7 (cationic amino acid transporter, γ+ system), member 1 (SLC7A1);
(B) generating, using a regression model equation which is LOGIT Ia=(200640_at)×4.6445+(200910_at)×(−4.9525)+(202397_at)×3.6645+(208114_s_at)×5.4097+(208699_x_at)×2.9153+(212247_at)×2.2052+(213175_s_at)×3.4262+(214431_at)×(−3.4637)+(222011_s_at)×4.4282−183.906;

LOGIT Ib=(201892_s_at)×2.0433+(215157_x_at)×3.0064+(217870_s_at)×2.1101+(218973_at)×4.07+(221494_x_at)×(−3.6926) −79.0097;

LOGIT II=(200976_s_at)×(−3.8876)+(205434_s_at0×(−1.8483)+(211974_x_at)×(−3.3451)+(213408_s_at)×(−3.8384)+(217917_s_a)×(−5.3073)+(221971_x_at)×7.0464+126.459;

LOGIT IIIa=(201123_s_at)×0.8651+(201642_at)×3.9114+(202301_s_at)×7.9516+(206544_x_at)×(−1.8805)+(208698_s_at)×2.8301+(211115_x_at)×4.0432+(211575_s_at)×(−4.3726)+(211913_s_at)×(−2.2606)−117.98;

LOGIT IIIb=(200880_at)×2.7955+(208765_s_at)×2.1072+(209157_at)×2.2478+(212398_at)×3.4807−104.518;

LOGIT IVa=(201178_at)×(−2.6194)+(212911_at)×(−2.4526)+(213254_at)×(−1.7758)+(217969_at)×2.475+(218659_at)×3.3188+(64418_at)×(−2.4296)+22.4303;

LOGIT IVb=(202211_at)×(−2.1207)+(212884_x_at)×(−1.0461)+(221269_s_at)×(−0.9598)+40.9722;

LOGIT V=(200921_s_at)×(−2.6385)+(201057_s_at)×(−2.5845)+(207335_x_at)×(−2.7044)+(209584_x_at)×(−1.6973)+(211733_x_at)×(−4.2067)+(217118_s_at)×(−2.539)+171.7096;

LOGIT VI=(201266_at)×2.5851+(202905_x_at)×2.7306+(203006_at)×1.6767+(206559_x_at)×13.1357+(212295_s_at)×2.7269−286.114, a set of logit scores for each of nine gene clusters, wherein said clusters comprise:
(a) cluster 1a comprises genes i-ix;
(b) cluster 1b comprises genes x-xiv;
(c) cluster 2comprises genes xv-xx;
(d) cluster 3a comprises genes xxi-xxviii;
(e) cluster 3b comprises genes xxix-xxxii;
(f) cluster 4a comprises genes xxxiii-xxxviii;
(g) cluster 4b comprises genes xxxix-xli;
(h) cluster 5comprises genes xlii-xlvii; and
(i) cluster 6comprises genes xlviii-lii;
(C) applying said logit scores to generate a predictive rule using a k-nearest neighbors classification method;

(D) evaluating the expression profile of the 12 genes which are (i) non-POU domain containing, octamer-binding (NONO);
  (ii) transketolase (TKT);
  (iii) IMP (inosine monophosphate) dehydrogenase 2 (IMPDH2);
  (iv) glutamyl-prolyl-tRNA synthetase (EPRS);
  (v) eukaryotic translation initiation factor 3, subunit12 (EIF3S12);
  (vi) chaperonin containing TCP1, subunit 2 β (CCT2);
  (vii) chaperonin containing TCP1, subunit 3 γ (CCT3);
  (viii) chaperonin containing TCP1, subunit 1 α (TCP1);
  (ix) anaphase promoting complex subunit 5 (ANAPC5);
  (x) nucleolar guanine nucleotide binding protein-like 2 (GNL2);
  (xi) RNA binding motif protein 28 (RBM28); and
  (xii) hypothetical protein FLJ12671 (FLJ12671);
using the predictive rule $$[\text{Probability for low risk of distant metastasis}] = \frac{1}{1 + e^{-(logit\ score)}}$$

wherein the logit score is generated based on the expression profiles of said 12 genes using a regression model equation which is logit($\pi$)=459.9+(200057_s_at)×(−12.5305)+(200842_s_at)×12.3230+(200910_at)×21.4064+(201892_s_at)×(−10.5046)+(201947_s_at)×20.0446+(201948_at)×(−17.7163)+(208114_s_at)×(−35.1981)+(208699_x_at)×(−13.8378)+(208722_s_at)×(−11.2409)+(218593_at)×(−15.2664)+(221494_x_at)×25.3464+(222011_s_at)×(−22.8465);

and
said logit score is correlated with risk of distant metastasis using the eauation $$\eta = \text{log}it(\pi) \equiv \log\left(\frac{\pi}{1-\pi}\right) = \alpha + \beta' X,$$

which is estimated by $$\hat{\eta} = \hat{\alpha} + \hat{\beta}' X \Rightarrow \hat{\pi} = \frac{1}{1 + e^{-\hat{\eta}}},$$

wherein,
$\eta$ is logit score;
$\pi$ is probability for low risk of distant metastasis;
$\alpha$ is a constant;
$\beta$ is coefficient;
X is normalized intensity of each probe set; and
(E) comparing the risk results from the two predictive rules; wherein if the risk of distant metastasis determined from both of said methods is low or high, then the risk is scored as low or high, respectively, and if said determined risks are discordant, then the risk is scored as indeterminate.

* * * * *

UNITED STATES PATENT AND TRADEMARK OFFICE
CERTIFICATE OF CORRECTION

PATENT NO. : 7,998,674 B2
APPLICATION NO. : 12/067549
DATED : August 9, 2011
INVENTOR(S) : Kuo-jang Kao et al.

It is certified that error appears in the above-identified patent and that said Letters Patent is hereby corrected as shown below:

Column 38, Line 6 reads: "t-complex 1 (TCP1);" should read --(viii) t-complex 1 (TCP1);--.

Column 38, Line 22 reads: "phosphatidylinosito 4-kinase, catalytic, alpha polypeptide" should read --(xviii) phosphatidylinositol 4-kinase, catalytic, alpha polypeptide--.

Column 38, Line 29 reads: "non-POU domain containing, octamer-binding (NONO);" should read --(xxiii) non-POU domain containing, octamer-binding (NONO);--.

Column 40, Line 43 reads: "(viii) chaperonin containing TCP1, subunit 1 α a" should read --(viii) chaperonin containing TCP1, subunit 1 α--.

Column 42, Line 67 reads: "(INPP5A); and" should read --(INPP5A); or--.

Column 43, Line 7 reads: "transketolase (TKT);" should read --(ii) transketolase (TKT);--.

Column 43, Line 20 reads: "(xi) RNA binding motif protein 28 (RBM28); and" should read --(xi) RNA binding motif protein 28 (RBM28); or--.

Column 44, Line 42 reads: "(INPP5A); and" should read --(INPP5A); or--.

Column 44, Line 60 reads: "(xi) RNA binding motif protein 28 (RBM28); and" should read --(xi) RNA binding motif protein 28 (RBM28); or--.

Column 46, Line 26 reads: "LOGIT II=(200976_s_at)x(-3.8876)+(205434_s_at0x" should read -- LOGIT II=(200976_s_at)x(-3.8876)+(205434_s_at)x--.

Column 46, Line 59 reads: "(c) cluster 2comprises genes xv-xx;" should read --(c) cluster 2 comprises genes xv-xx;--.

Signed and Sealed this
Twenty-eighth Day of February, 2012

David J. Kappos
*Director of the United States Patent and Trademark Office*

CERTIFICATE OF CORRECTION (continued)
U.S. Pat. No. 7,998,674 B2

Column 46, Line 64 reads: "(h) cluster 5comprises genes xlii-xlvii; and" should read
--(h) cluster 5 comprises genes xlii-xlvii; and--.

Column 46, Line 65 reads: "(i) cluster 6comprises genes xlviii-lii;" should read
--(i) cluster 6 comprises genes xlviii-lii;--.